United States Patent [19]

Moady et al.

[11] Patent Number: 5,955,081
[45] Date of Patent: Sep. 21, 1999

[54] ANTIPSORIATIC COMPOSITIONS, METHOD OF MAKING, AND METHOD OF USING

[76] Inventors: Marzook Moady, deceased, late of Yarka Village; by Naseba Moady, heir, Yarka Village 24967, both of Israel

[21] Appl. No.: 08/621,043

[22] Filed: Mar. 22, 1996

[51] Int. Cl.⁶ .................................................. A61K 35/78
[52] U.S. Cl. ..................... 424/195.1; 514/685; 514/863
[58] Field of Search ...................... 424/195.1; 514/863, 514/685

[56] References Cited

U.S. PATENT DOCUMENTS 3,881,000  4/1975  Freidmann et al. ............... 514/105
5,091,181  2/1992  Papadakis et al. ................ 424/195.1

OTHER PUBLICATIONS

F. M. Hammouda, et al., Anthraquinones of Certain Egyptian Asphodelus Species. Z. Naturforsch. 29c 351–354, 1974.

"Therapeutic Botanicol Protocal for Psoriasis", Richard Scalzo, Helen Batchelder, Dr. Xiping Wang, and Dr. Jay Glaser, *Protocol Journal of Botanical Medicines*, Autumn 1994, pp. 1–38.

"Forestomach Papillomas in Flaky Skin and Steel–Dickie Mutant Mice", John P. SUndberg, George A. Kenty, Wesley G. Beamer and Daniel L. Adkinson, *J Vet Diagn Invest* 4:312–317 (1992), From The Jackson Laboratory, 600 Main St, Bar Harbor, ME 04609, Received for publication Oct. 7, 1991.

"Epidermal Dendritic Cell Populations in the Flaky Skin Mutant Mouse", John P. Sundberg, Dawnalyn Boggess, Beth A. Sundberg, Wesley G. Beamer and Leonard D. Shultz, *Immunol Invest* 22:389–401 (1993), Abstract From The Jackson Laboratory, 600 Main St, Bar Harbor , ME 04609.

"Antipsoriatic Anthrones with Modulated Redox Properties", K. Muller, P. Leukel, K. Zieris and I. Gawlik, *J Med Chem* 37(11):1660–9 (May 27, 1994), Abstract from the Universitate Regensburt, Institut fur Pharmazie, Germany.

*Primary Examiner*—Jean C. Witz
*Attorney, Agent, or Firm*—Allen, Dyer, Doppelt, Milbrath & Gilchrist, P.A.

[57] ABSTRACT

A psoriasis treatment composition derived from the plant *Asphodelus Microcarpus* includes 3-methylanthralin, chrysophanol, aloe-emodin, aloe-emodin monoacetate, and/or derivatives thereof. The composition is prepared by extracting a liquid from the *Asphodelus Microcarpus* root and mixing the liquid with acetic acid. A method of treatment includes applying the composition to an affected area of skin at a frequency sufficient to effect an alleviation of symptoms, typically once per day for 14–56 days.

13 Claims, 24 Drawing Sheets

ANTIPSORIATIC COMPOSITIONS, METHOD OF MAKING, AND METHOD OF USING

BACKGROUND OF INVENTION

1. Field of the Invention

The present invention relates to skin treating compositions, to a method of making the compositions, and to a method of using the compositions in the treatment of skin. In another aspect, the present invention relates to antipsoriasis compositions, to a method of making the compositions, and to a method of using the compositions to treat psoriasis. In even another aspect, the present invention relates to botanical-derived skin treating compositions, to a method of making the compositions, and to a method of using the compositions to treat skin.

2. Description of the Related Art

Psoriasis is a chronic skin condition characterized by itchy, flaky skin. It is estimated that two percent of the United States population, more than four million people, will suffer from psoriasis during their lives. Psoriasis conditions can range from mild to severe.

In the United States, between about 150,000 and 250,000 new cases of psoriasis occur each year, with about 40,000 of these cases classified as severe. Sufferers of psoriasis must endure not only the irritating disease itself, but also the embarrassment of skin disfigurement.

The total annual cost for treating psoriasis on an outpatient basis is estimated at more than $1.5 billion. It is estimated that psoriasis sufferers are spending an average of $500 per year on psoriasis treatment to achieve only temporary relief. Severe cases that require hospitalization may require an expenditure of up to $10,000.

The compound 3-methylanthralin has long been utilized in the treatment of psoriasis, and is listed in the *Merck Index* as an antipsoriatic. Chrysarobin is a mixture of compounds derived from Goa powder, and includes 3-methylanthralin. Goa powder itself is derived from the wood and bark of Andria Araroba Aguiar (Fam. Leguminosae). Literature references describing the isolation of and structure of Chrysarobin date back to the early 1800s. A method of reducing Chrysarobin to obtain 3-methylanthralin was known as early as 1931.

Known psoriasis treatments include: antimetabolites such as methotrexate; corticosteroids such as triamcinolone creams or injection, clobeasol propinate cream, and hydrocortisone; keratolytic/destructive agents such as anthralin or salicylic acid; lubricants such as hydrogenated vegetable oils and white petroleum; oral retinoids such as etretinate or isotretinoin tablets; photochemotherapy such as methoxsalen or trioxsalen capsules, and coal tar; and topical cholecalciferol analogs such as calcipotriene ointment, a topical vitamin D3, known commercially as Dovonex®, (Squib, Buffalo, N.Y.).

Numerous botanical protocols for the treatment of psoriasis are known, including the use of extracts of various herbs, roots, seeds, flowers, berries, and twigs. See *Therapeutic Botanical Protocol for Psoriasis,* Protocol Journal of Botanical Medicines, August 1994, pp. 1–38.

However, the known psoriasis treatments suffer from one or more deficiencies, including potential toxic side effects and achieving only temporary relief. Thus there is a need for improved psoriasis treatment.

SUMMARY OF INVENTION

It is an object of the present invention to provide a composition and method of treating psoriasis.

It is another object of the present invention to provide a method for making 3-methylanthralin.

It is even another object of the present invention to provide a method of making chrysophanol.

It is still another object of the present invention to provide a method of making aloe-emodin.

It is a further object to provide a method of making aloe-emodin monoacetate.

It is an additional object to provide a composition extracted from a botanical specimen that has efficacy in treating psoriasis.

It is another object to provide such a composition having a plurality of polyphenols therein.

It is a further object to provide a method of treating psoriasis with such a composition.

It is yet another object to provide a method of extracting such a composition from the botanical specimen.

These and other objects of the present invention are achieved by the composition and methods of the present invention.

According to even still another embodiment of the present invention there is provided a method of making a product comprising at least one of 3-methylanthralin, chrysophanol, aloe-emodin, and aloe-emodin monoacetate comprising contacting root of the plant *Asphodelus Microcarpus* with acetic acid to form the product. A further embodiment of the method includes recovering 3-methylanthralin, chrysophanol, aloe-emodin, or aloe-emodin monoacetate from the product. Any of the products may be further derivatized.

According to yet even another embodiment of the present invention there is provided a method of obtaining either 3-methylanthralin, chrysophanol, or aloe-emodin by recovery of the desired compound from the root of the plant *Asphodelus Microcarpus*. The polyphenols may be further derivatized.

DETAILED DESCRIPTION OF THE INVENTION

Figure 1:
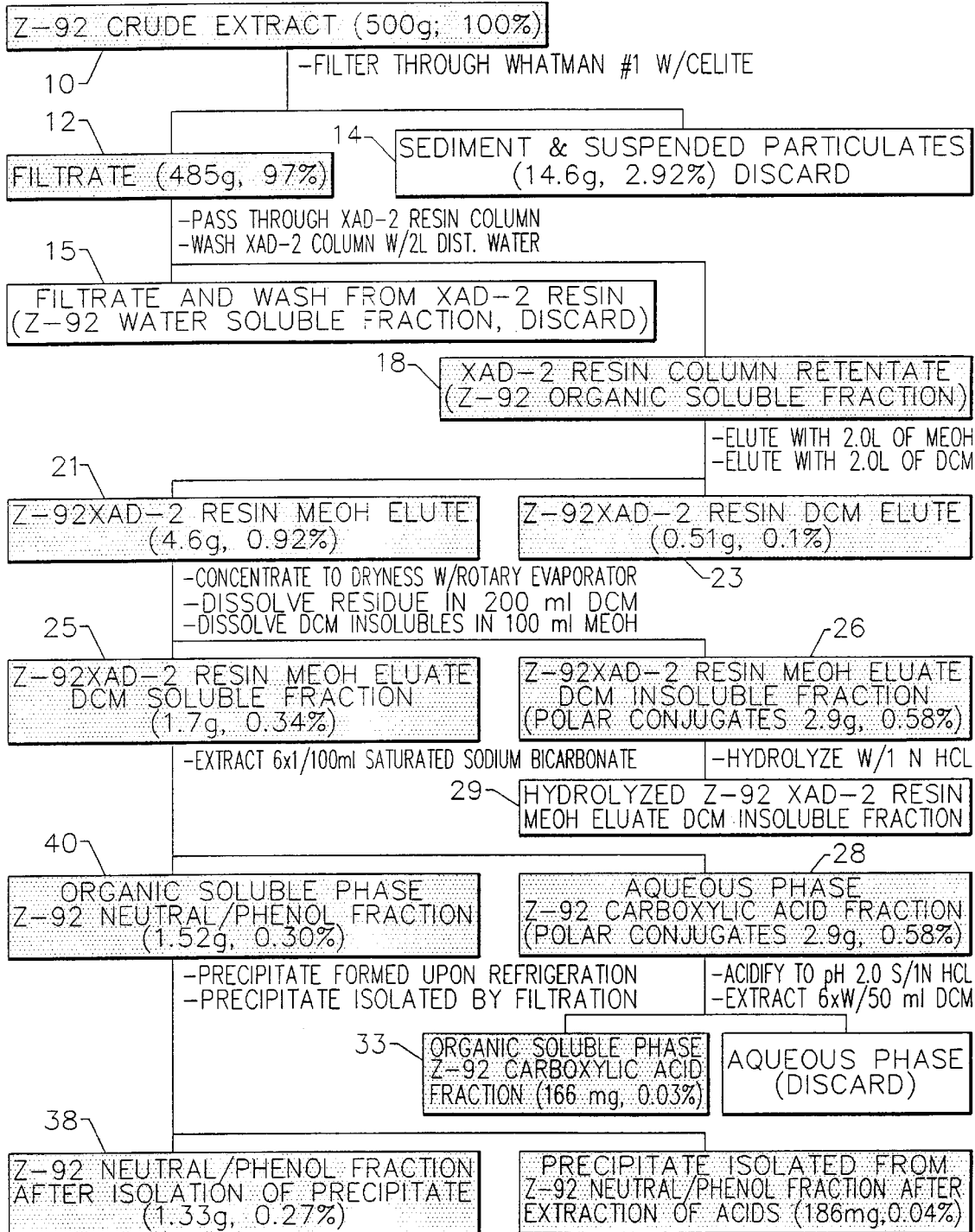
FIG. 1 is a schematic representation of the analytical fractionation scheme utilized in Example 4.

In the practice of the present invention, a composition is made from the plant *Asphodelus Microcarpus* that comprises compounds useful in the treatment of mammalian skin disorders, especially psoriasis. *Asphodelus Microcarpus* is a plant that is native to the Middle East; specifically, it can be easily found in the Northern regions of Israel, as well as in regions from the Canary Islands to Asia Minor.

In the practice of the present invention, the root of *Asphodelus Microcarpus* is utilized. In a specific embodiment of the present invention, the root or portions thereof may be administered to treat mammalian skin disorders. Preferably, in such a treatment, the outer skin of the root is first removed, and then the inner portion of the root is applied to the afflicted skin region. Additionally, raw extract from the roots may also be applied to the afflicted skin region.

It is to be understood in the practice of the present invention that the roots of *Asphodelus Microcarpus* may be harvested at any time. However, it is preferred that the roots be harvested at a time when they are full of liquid which for *Asphodelus Microcarpus* growing in Israel is generally from February to May.

Preparation of the *Asphodelus Microcarpus* roots is generally as follows. Excess dirt and other foreign matter should be removed from the roots, generally by shaking and water washing. After dirt and other foreign matter have been removed from the root, the next step is to remove the outer layer of the root. This can be accomplished by using a scraper, knife, a peeler such as a potato peeler, or the like.

The next step is to extract liquid from the roots. Methods for obtaining liquid from a compressible liquid-containing solid are well known to those of skill in the art, and any such method may be utilized. Simple methods include mashing, squeezing, pulverizing, liquefying, or compressing the roots. Preferably, the roots are liquefied in a commercially available "juicer."

The liquid thus obtained is mixed with acetic acid. Generally for this step, the volume ratio of *Asphodelus Microcarpus* root juice to acetic acid is in the range of about 1:20 to about 20:1. Preferably, the volume ratio is in the range of about 1:10 to about 10:1, more preferably in the range of about 1:5 to about 5:1, even more preferably approximately 4:1.

The *Asphodelus Microcarpus* root liquid is next mixed with acetic acid at any temperature suitable for creating a mixture of 3-methylanthralin, chrysophanol, aloe-emodin, and aloe-emodin monoacetate. It is preferable that the mixing occur with both the *Asphodelus Microcarpus* root liquid and acetic acid in the liquid state. Thus the contacting temperature is above the freezing point but below the boiling point for the mixture.

Optionally, in the practice of the present invention, brimstone may be mixed in with the *Asphodelus Microcarpus* root and acetic acid. The brimstone may be in any suitable form, but is preferably ground, and more preferably ground to a flour-like consistency.

The *Asphodelus Microcarpus* root/acetic acid mixture comprises 3-methylanthralin, chrysophanol, aloe-emodin, and aloe-emodin monoacetate and has been shown to be useful in the treatment of psoriasis. While this mixture is shown herein as being derivable from the *Asphodelus Microcarpus* root, it should be understood that the 3-methylanthralin, chrysophanol, and aloe-emodin can be obtained by the methods that are known in the art. Aloe-emodin monoacetate can be made by contacting aloe-emodin with acetic acid.

3-Methylanthralin, chrysophanol, aloe-emodin, and aloe-emodin monoacetate can be individually recovered from the mixture using separation techniques as are well known in the art.

The treatment composition of the present invention may include a wide range of the polyphenol components and/or their derivatives. In the method of the present invention for treating psoriasis, the composition may be administered to a mammalian organism by any route known in the art. Non-limiting examples of suitable routes of administration include oral, parenteral, topical, and the like. Specific non-limiting examples of carrying out such routes of administration include injection, IV administration, pills, tablets, capsules, liquids, gels, creams, soaps, shampoos, dermal patches, inhaled aerosols, sprays, suppositories, and the like. Topical administration is preferred for human psoriasis.

The frequency of administration varies with the strength of the composition, but an exemplary treatment schedule comprises a topical application once per day until symptoms are eradicated. The course of treatment naturally is dependent upon the severity of the affliction, and may last from 14 days up to 56 days, although this is not intended as limiting.

The present invention is described as being suitable for the treatment of humans for psoriasis, which is to be understood to include, but not be limited to, exfoliative psoriatic dermatitis, pustular psoriasis, and guttatte variant psoriasis.

It is also believed that the compositions of the present invention are useful in the treatment of other skin disorders and conditions, including eczema.

In addition to being used in the treatment of skin disorders, the compositions of the present invention are also believed to be useful in the treatment of psoriatic arthritis.

EXAMPLES

The following examples are provided merely to illustrate the invention and are not intended to limit the scope of the invention in any manner.

Example 1

Obtaining Raw Extract

Raw extract was obtained from the *Asphodelus Microcarpus* plant as follows. Approximately 1 lb of roots of the plant were obtained from a location in Israel. Dirt and other foreign matter was removed from the roots by shaking, and then by washing with water, after which the outer skin of the roots was removed. Liquid was extracted from the peeled roots utilizing a commercially available "juicer". The 1 lb of roots yielded approximately 300 cc of raw extract.

Example 2

Preparation of Treatment Solution

Approximately 650 cc (although 400–800 cc are usable, depending upon the severity of the affliction) of the raw extract obtained by the method of Example 1, approximately 350 cc (although 200–600 cc are usable) of acetic acid, and approximately 1 teaspoon of brimstone, ground to flour-like texture, were mixed together. This mixture does not require refrigeration, although the raw extract should be refrigerated until the acetic acid is introduced if kept in an unmixed state.

Example 3

Analysis of the Treatment Solution

The treatment solution of Example 2 was subjected to various types of chemical and physical analysis, the results of which are presented in Tables 1 and 2.

TABLE 1

Proximate Analysis Data*

| Physical description of sample | Dark brown liquid containing sediment and suspended particulate matter, acetic acid like odor |
|---|---|
| Ph (as received) | 1.95 |
| Acetic acid content (by titration) | 5.05% w/w |
| Insoluble matter | 2.14% w/w |
| Ash weight (mineral content) | 0.746% w/w |
| Specific gravity (filtrate) | 1.103 g/ml |
| Total dissolved solids (filtrate) | 12.94% w/w |
| Chloroform extractables (filtrate) (organic soluble components) | 0.84% w/w |

*Analysis performed by Stillwell & Gladding Testing Laboratories, Inc., New York, N.Y.

TABLE 2

Elemental/Heavy Metal Composition*

| Element | Conc. ppm |
|---|---|
| Sulfur | 4260 |
| Potassium | 1640 |
| Calcium | 1075 |
| Sodium | 216 |
| Phosphorous | 142 |
| Magnesium | 100 |
| Silicon | 7 |
| Iron | 7 |
| Aluminum | 5 |
| Zinc | 2 |
| Tin | 1 |
| Strontium | 0.9 |
| Copper | 0.9 |
| Manganese | 0.4 |
| Titanium | 0.4 |
| Nickel | 0.4 |
| Chromium | 0.2 |
| Barium | 0.1 |
| Vanadium | 0.06 |
| Bismuth | ND < 3 ppm |
| Lead | ND < 3 ppm |
| Antimony | ND < 3 ppm |
| Boron | ND < 2 ppm |
| Indium | ND < 2 ppm |
| Molybdenum | ND < 1 ppm |
| Arsenic | ND < 1 ppm |
| Selenium | ND < 1 ppm |
| Tellurium | ND < 1 ppm |
| Thallium | ND < 1 ppm |
| Lithium | ND < 1 ppm |
| Cobalt | ND < 1 ppm |
| Niobium | ND < 1 ppm |
| Gallium | ND < 1 ppm |
| Germanium | ND < 1 ppm |

TABLE 2-continued

Elemental/Heavy Metal Composition*

| Element | Conc. ppm |
|---|---|
| Silver | ND < 1 ppm |
| Cadmium | ND < .5 ppm |
| Mercury | ND < .5 ppm |
| Beryllium | ND < .1 ppm |

*Elemental/heavy metal analysis was conducted by Umpire and Control Services, Inc., West Babylon, N.Y.

Example 4

Fractionation of Treatment Solution

The solution of Example 2 was also subjected to analysis. As the solution of Example 2 is too complex for direct analysis, it was fractionated according to the scheme in FIG. 1 using a combination of wet analytical chemistry, column chromatography and solvent extraction procedures. Throughout the analytical fractionation, isolates were subjected to cell culture bioassay, as described in Example 6. Fractions testing positive in the cell culture bioassay were then directed to additional separation and/or chemical characterization until nearly pure isolates were obtained.

A 500 g sample 10 of the treatment solution of Example 2 was filtered through a Buchner funnel containing Whatman #1 filter paper and a 1 cm bed volume of Celite® analytical filtering aid. The filtrate 12 (485 g, 97% of original sample) tested positive in the cell culture bioassay and was equivalent in potency to the unfiltered treatment solution of Example 2. The filter retentate 14 (14.6 g, 2.92%) was a dark reddish brown colored material with a clay-like consistency. This substance tested negative in the cell culture bioassay. Analysis of this sediment indicates it to be largely composed of sucrose, complex carbohydrates, cellulosic debris, lignins, inorganic minerals, and clay.

The filtrate was then passed through a preconditioned chromatographic column packed with a 20×350 mm bed volume of XAD-2 resin. (Supelcopak-2® absorbent) at a flow rate of 5 ml/minute. XAD-2 resin is a hydrophobic porous polymer absorbent based on styrene-divinylbenzene copolymer. This resin has a high affinity for absorbing nonpolar, organic-soluble components from aqueous solutions. The column was preconditioned by washing it with 1.0 L of dichloromethane (DCM), followed by 1.0 L of methanol (MeOH) and finally 1.0 L of distilled/deionized water. All solvents were ultra-high-purity "capillary-analyzed" grade suitable for trace-level chemical analysis procedures. The distilled water used throughout the analysis was obtained from a Milli-Q® purification system. It was double distilled in glass and then further purified by passing it through ion-exchange and activated carbon filters. After the filtrate was passed through the XAD-2 resin, the column was washed with 2 L of distilled water. The filtrate and wash 15 from the XAD-2 resin column tested negative in the call culture bioassay and were discarded. This dark brown colored fraction contains the water-soluble compounds of the treatment solution, such as acetic acid, sugars, low-molecular-weight polar organic acids, tannins, and other biologically inert components.

The XAD-2 resin column containing the treatment solution retentate 18 was blown dry to remove as much of the residual wash water as possible. The treatment solution organic-soluble components were then eluted from the column with 2.0 L of MeOH followed by 2.0 L of DCM. The MeOH and DCM XAD-2 resin eluates were collected separately. The treatment solution XAD-2 resin MeOH eluate 21 yielded 4.6 g, which corresponds to 0.92% of the original treatment solution on a weight basis. The eluate was amber colored. The treatment solution XAD-2 resin DCM eluate 23 contained 0.51 g or 0.1 of the original sample. This eluate was bright yellow colored. Both of these fractions tested positive in the cell culture bioassay. However, higher activity was observed in the treatment solution XAD-2 resin MeOH eluate. Therefore, this isolate was subjected to additional fractionation.

The treatment solution XAD-2 resin MeOH eluate 21 was concentrated to dryness in a round bottom flask using a rotary evaporator at reduced temperature and pressure. The residue was a dark red crystalline substance. The residue was dissolved in 200 ml of DCM, producing an amber-colored solution. However, not all the residue was soluble in DCM. The DCM-insoluble materials were then dissolved in 100 ml of MEOH. The methanol-soluble components had a dark red color. Thus two additional fractions were prepared. The treatment solution XAD-2 resin MEOH eluate DCM-soluble fraction 25 contained 1.7 g (0.34%), and the treatment solution XAD-2 resin MeOH eluate DCM-insoluble fraction 26 yielded 2.9 g (0.58%). Both of these fractions tested positive in the cell culture bioassay.

The treatment solution XAD-2 resin MEOH eluate DCM-soluble fraction 40 contains organic-soluble neutral, phenolic, and acidic components. It was extracted 6 times with 100 ml portions of saturated sodium bicarbonate solution to remove the carboxylic acid fraction. The saturated sodium bicarbonate extract 28 was acidified to Ph 2.0 using 1 N HCL and then back-extracted 6 times with 50 ml portions of DCM to partition the carboxylic acids into the organic phase. The treatment solution carboxylic acid fraction 33 contained 166 mg (0.03%) and was weakly positive in the cell culture bioassay. The fraction had an amber-colored appearance.

The treatment solution XAD-2 resin MeOH eluate DCM-soluble fraction, after extraction of the carboxylic acids, contained 1.52 g or 0.30% of the original sample. This isolate 31 was named the treatment solution "neutral/phenol fraction" based on its chemical composition. It yielded a strong positive response in the cell culture bioassay. Upon refrigeration this fraction was observed to form a yellow-orange-colored crystalline precipitate. The precipitate was isolated by filtration through a sintered glass type Gooch crucible. The precipitate 36 isolated from the neutral/phenol fraction after extraction of acids yielded 186 mg (0.04%) of bright yellow-orange crystals. This isolate was found to be the most highly active fraction in the cell culture bioassay. The neutral/phenol fraction 38 after harvesting of the crystalline precipitate was found to contain 1.33 g (0.27%). This sample also tested strongly positive in the cell culture bioassay.

Some additional subfractions were prepared from the isolates described above. A portion of the treatment solution carboxylic acid fraction was methylated with diazomethane reagent to produce the corresponding methyl esters of the sample. This was done to enhance the volatility of the acids to improve the gas chromatographic separation. The treatment solution XAD-2 resin MeOH eluate DCM-insoluble fraction was hydrolyzed with 1 N HCl for 4 hours at 100° C. to break down glycosidically conjugated species. The treatment solution neutral/phenol fraction 29 after harvesting of precipitate was subjected to additional minicolumn fractionation using a silica gel solid-phase extraction column. These procedures are described in more detail Example 5.

Example 5

Chemical Characterization of the Fractions of Example 4

The nonvolatile components of the fractions were analyzed by a combination of electron ionization direct probe mass spectrometry (DP data) and by a high-mass technique, liquid secondary ion mass spectrometry (LSIMS data).

Figure 2:
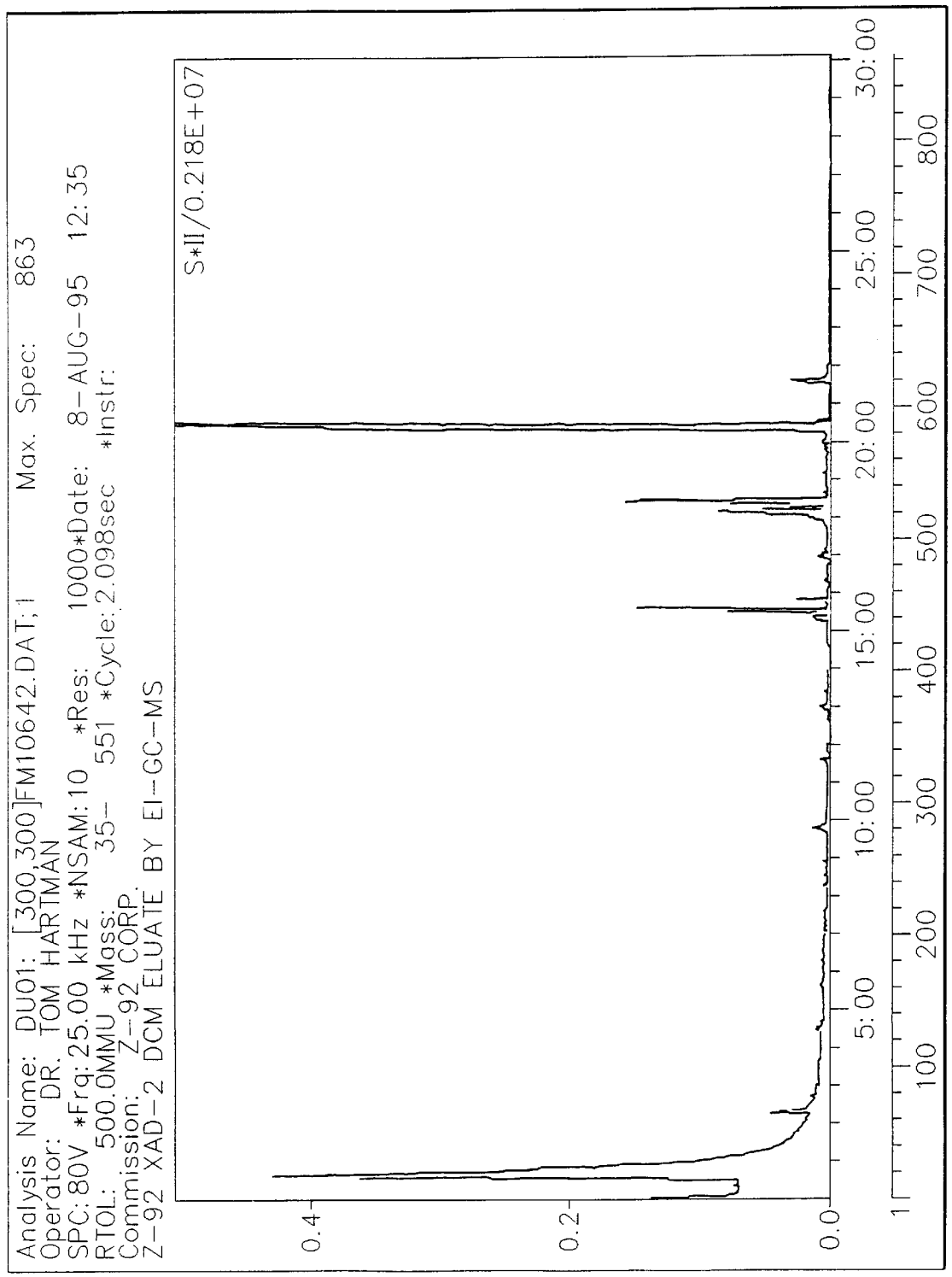
FIG. 2 shown the peak assignments used to generate the data of Table 3 for the XAD-2 resin DCM eluate fraction 23.
Figure 3:
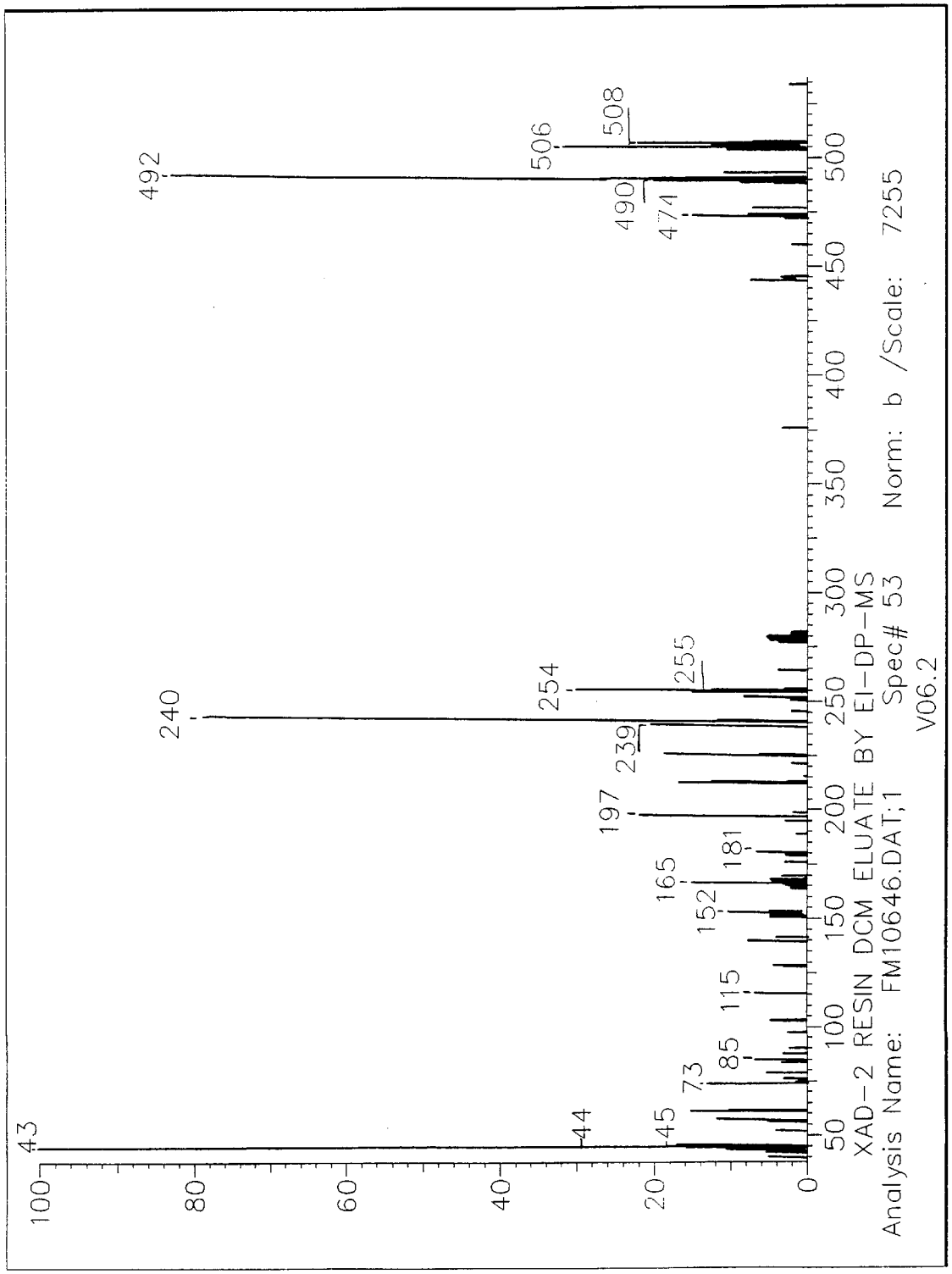
FIGS. 3 and 4, show, respectively, the direct probe (DP) mass spectrometry data and liquid secondary ion mass spectrometry (LSIMS) data pertaining to the XAD-2 resin DCM eluate fraction 23 of FIG. 1.
Figure 4:
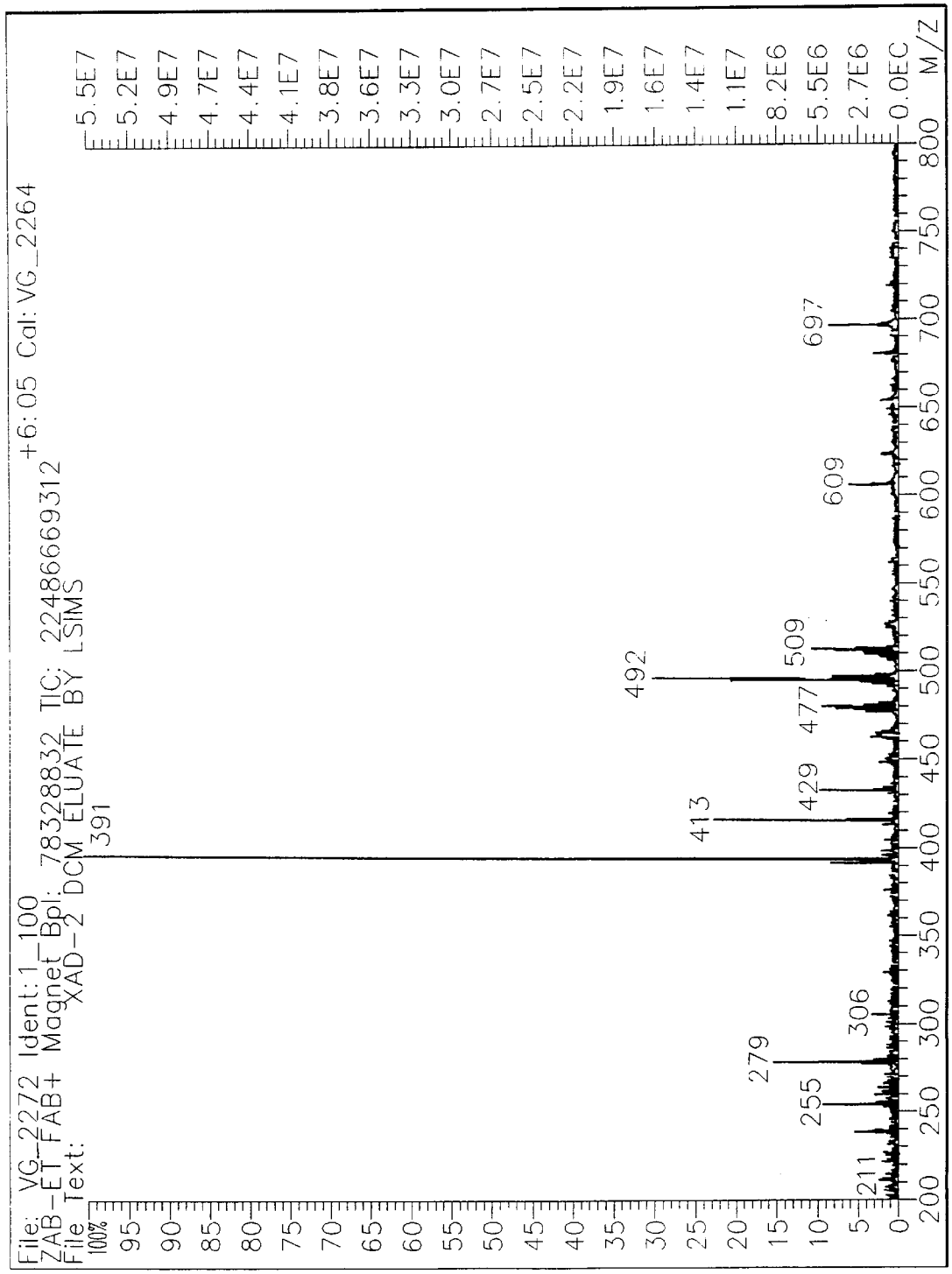

The chemical composition of the XAD-2 resin DCM eluate fraction 23 is shown in Table 3, with peak assignments corresponding to the GC-MS chromatogram shown in FIG. 2. The DP and LSIMS spectra pertaining to the XAD-2 resin DCM eluate fraction 23 are shown in FIGS. 3 and 4, respectively. A homologous series of nonvolatile compounds with molecular weights 474, 490, 506, and 508 were detected in the DP data. Accurate mass measurements were performed on these peaks using high-resolution (R=10,000) mass spectrometry in order to determine their elemental formulas. The empirical formulas for these compounds were found to be $C_{23}H_{22}O_{11}$ (474 MW), $C_{23}H_{22}O_{12}$ (490 MW), $C_{13}H_{22}O_{13}$ (506 MW), and $C_{23}H_{24}O_{13}$ (508 MW). In other fractions related homologues with molecular weights 478 and 492 were also observed. Exact chemical structures for these compounds are unknown. However, their elemental formulas and mass spectral fragmentation patterns indicate that they are a class of polyphenolic chemical compounds called bisflavanoids.

TABLE 3

Chemical Composition XAD-2 Resin DCM Eluate Fraction 23 of FIG. 1

| MS Spec # | Compound (Synonyms, Common Names, Comments, Etc.) | CAS # | Peak Area % |
|---|---|---|---|
| 66 | phenol | 108-95-2 | 1.43 |
| 282 | sulfur (elemental sulfur six membered ring) | NA | 0.90 |
| 372 | dibutylphthalate (plasticizer) | 84-74-2 | 0.29 |
| 441 | hexadecanoic acid (palmitic acid) | 57-10-3 | 0.11 |
| 445 | sulfur (S-8, cyclic sulfur, ortho-thrombic sulfur, molecular sulfur) | 10544-50-0 | 9.02 |
| 452 | 1-hexadecanol (hexadecyl alcohol) | 36653-82-4 | 0.81 |
| 485 | linoleic acid | 60-33-3 | 0.91 |
| 519 | 3-methyl-1,8,9-anthracenetriol (3-methylanthralin, Chrysarobin) | 491-59-8 | 5.86 |
| 527 | 1,8-dihydroxy-3-methyl-9,10-anthracenedione (Chrysophanol, Chrysophanic acid, 1,8-dihydroxy-3-methyl-1,8-anthraquinone) | 481-74-3 | 11.76 |
| 549 | 1,8-dihydroxy-3-(hydroxymethyl)-9,10-anthracenedione (Aloe-Emodin) | NA | 0.14 |
| 574 | 2,4-bis(dimethylbenzyl)-6-t-butylphenol | NA | 0.27 |
| 583 | di-2-ethylhexylphthalate (plasticizer) | 117-81-7 | 65.44 |
| 619– 622 | monoacetate derivative of 1,8-dihydroxy-3-(hydroxymethyl)-9,10-anthracenedione (Aloe-Emodin monoacetate) | NA | 2.23 |
| DP Data | bis-flavanoids with m.w.'s 474 ($C_{23}H_{22}O_{11}$), 490 ($C_{23}H_{22}O_{12}$), 506 ($C_{23}H_{22}O_{13}$) and 508 ($C_{23}H_{24}O_{13}$) exact chemicals structures unknown | NA | 1.73 (est. total for DP & LSIMS) |
| LSIMS Data | unknown high mass compounds m.w. 608 & 696 | NA | 1.73 (est. total for DP & LSIMS data) |

Figure 5:
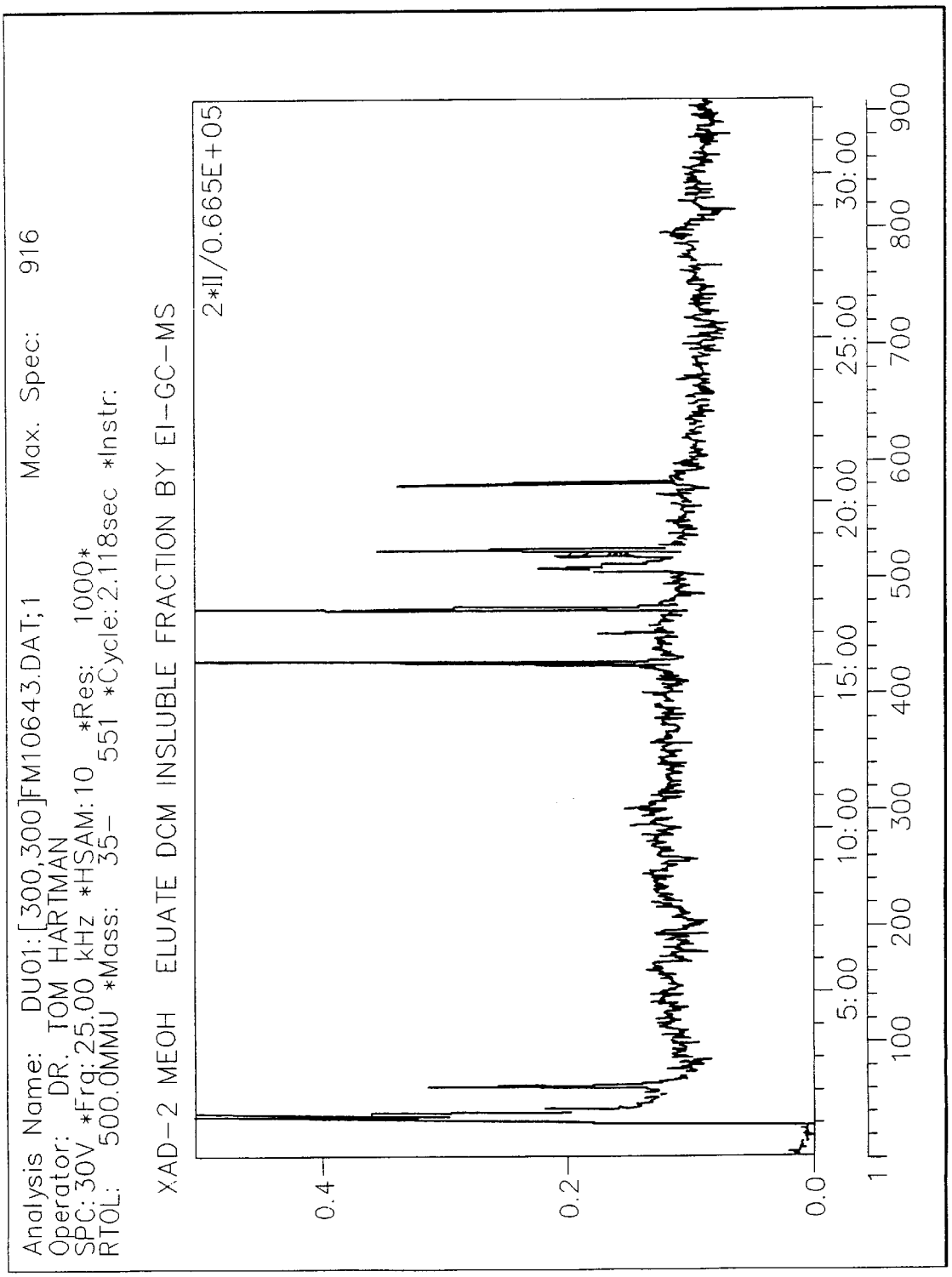
FIGS. 5, 6, and 7 show, respectively, a GC-MS chromatogram, DP data, and LSIMS data for the chemical composition of XAD-2 resin MeOH eluate DCM-insoluble fraction 26 of FIG. 1.
Figure 6:
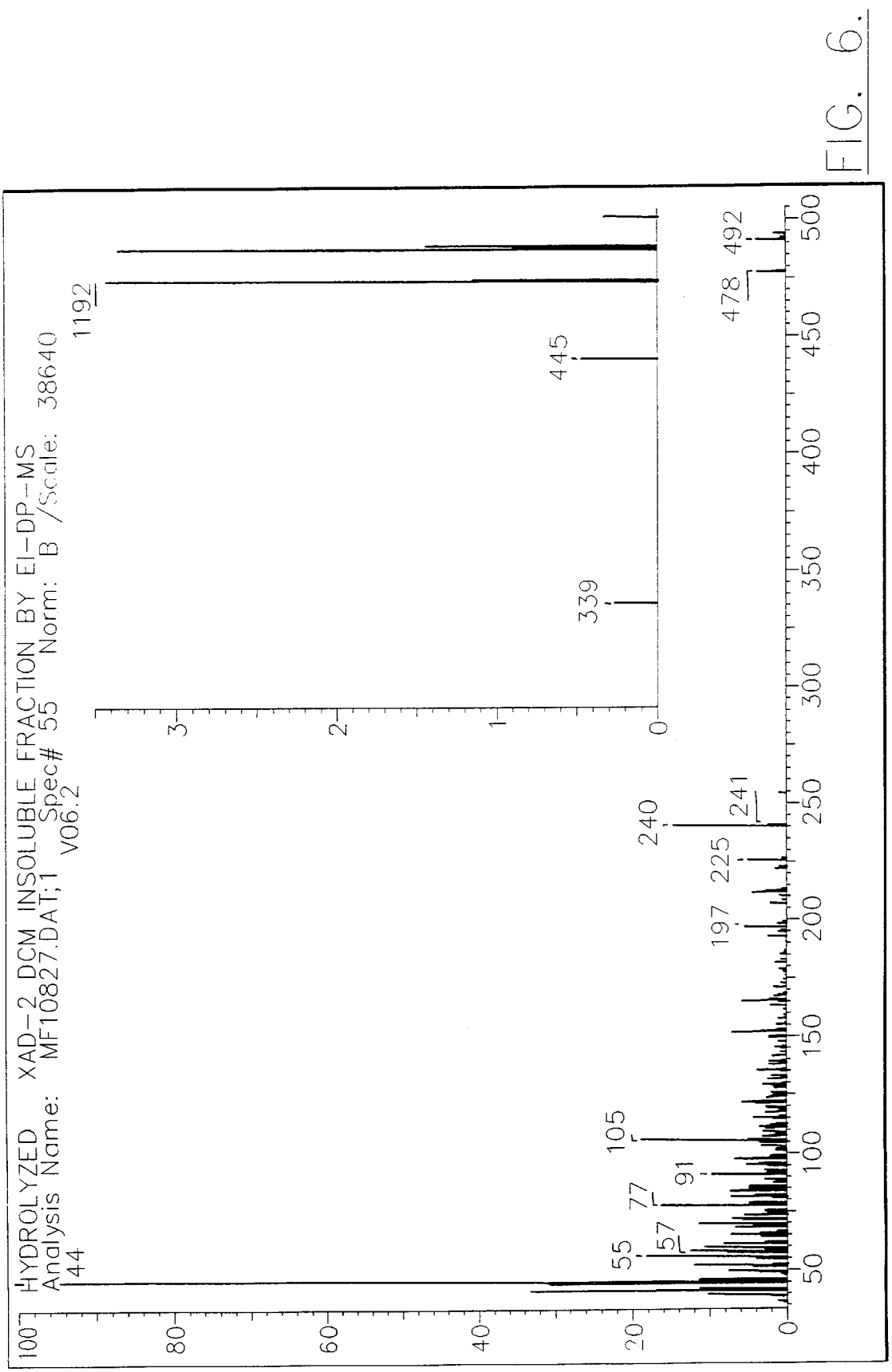
Figure 7:
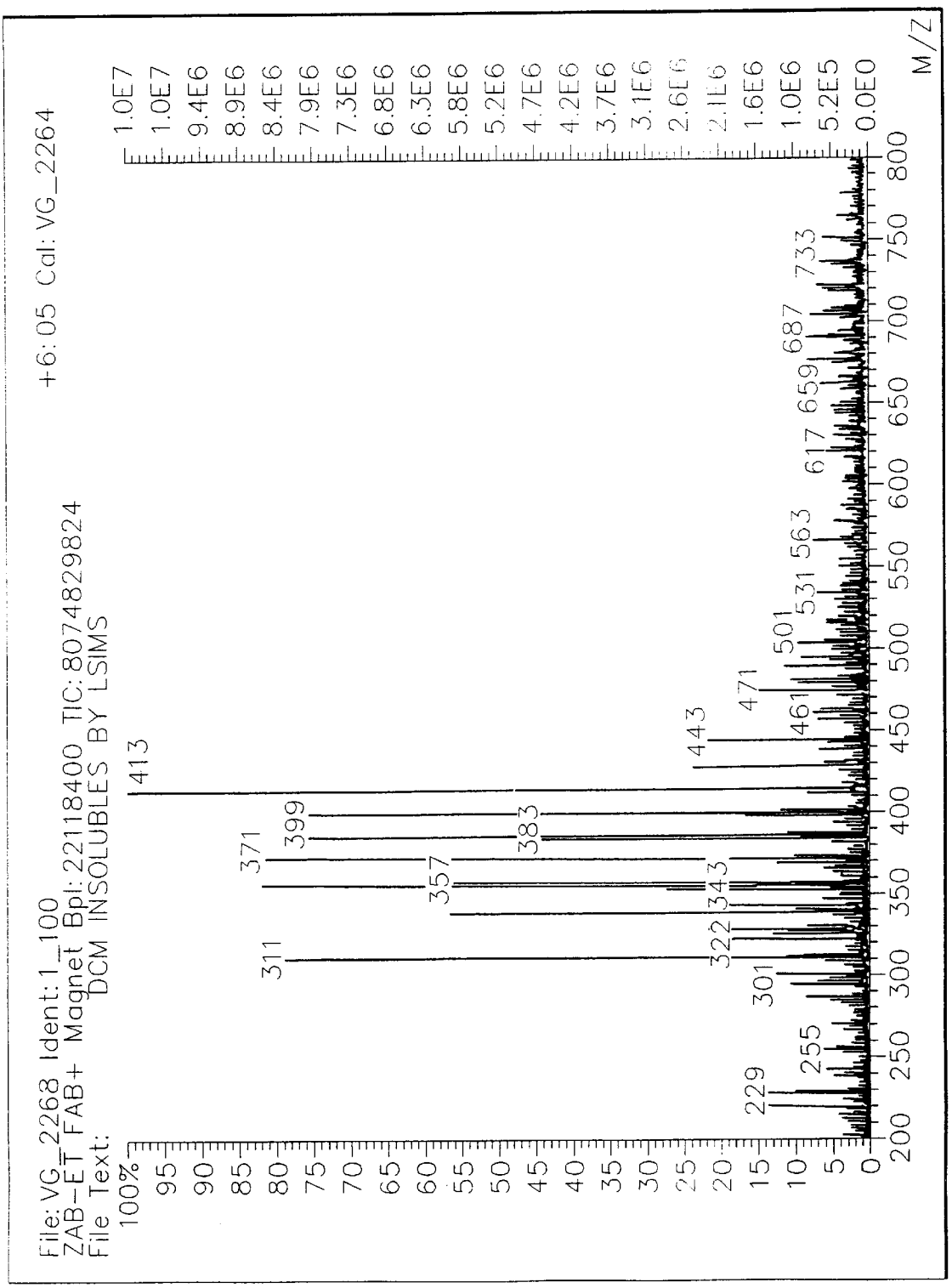

DP = Data is from Electron Ionization Direct Insertion Probe
LSIMS = Liquid Secondary Ion Mass Spectrometry The chemical composition of XAD-2 resin MeOH eluate DCM-insoluble fraction 26 is summarized in Table 4. The GC-MS chromatogram, DP data, and LSIMS data pertaining to this fraction are presented in FIGS. 5, 6 and 7. Most of this fraction was nonvolatile, and so the GC-MS peaks described make up only a small portion of this sample. The majority of the mass in this fraction consists of high-molecular-weight nonvolatile compounds. The DP data show relatively trace levels of several bisflavanoids. The LSIMS data show a complex mixture of high-mass compounds in the range 300–1000 to be present in this fraction. This fraction largely consists of "bound" compounds such as glycosides (phenolic compounds bound to sugar molecules) and other polar high-molecular-weight conjugates. This fraction was digested with HCl and heat in order to hydrolyze the conjugates down to small molecules, which could then be identified.

TABLE 4

Chemical Composition XAD-2 Resin MeOH Eluate DCM-Insoluble Fraction (Fraction 26 of FIG. 1)

| MS Spec # | Compound (Synonyms, Common Names, Comments, Etc.) | CAS # | Peak Area % |
|---|---|---|---|
| 423 | palmitic acid | 57-10-3 | 17.05 |
| 447 | unk. 216 m.w. aromatic | NA | 2.41 |
| 468 | linoleic acid | 60-33-3 | 28.08 |
| 519 | 3-methyl-1,8,9-anthracenetriol (3-methylanthralin, Chrysarobin) | 491-59-8 | 27.82 |
| 527 | 1,8-dihydroxy-3-methyl-9,10-anthracenedione (Chrysophanol, Chryso-phanic acid, 1,8-dihydroxy-3-methyl-1,8-anthraquinone) | 481-74-3 | 12.78 |
| 583 | di-2-ethylhexylphthalate (plasticizer) | 117-81-7 | 11.87 |
| DP Data | bis-flavanoids with m.w.'s 492 ($C_{23}H_{24}O_{12}$) and 506 ($C_{23}H_{22}O_{13}$) exact chemicals structures unknown | NA | trace |
| LSIMS Data | complex mixture of unknown compounds m.w. range 300–1000 (bound components, glycosides, high m.w. polar conjugates etc.) | NA | major |

DP = Data is from Electron Ionization Direct Insertion Probe raw data file FM10647
LSIMS = Liquid Secondary Ion Mass Spectrometry Data file VG2268

Figure 8:
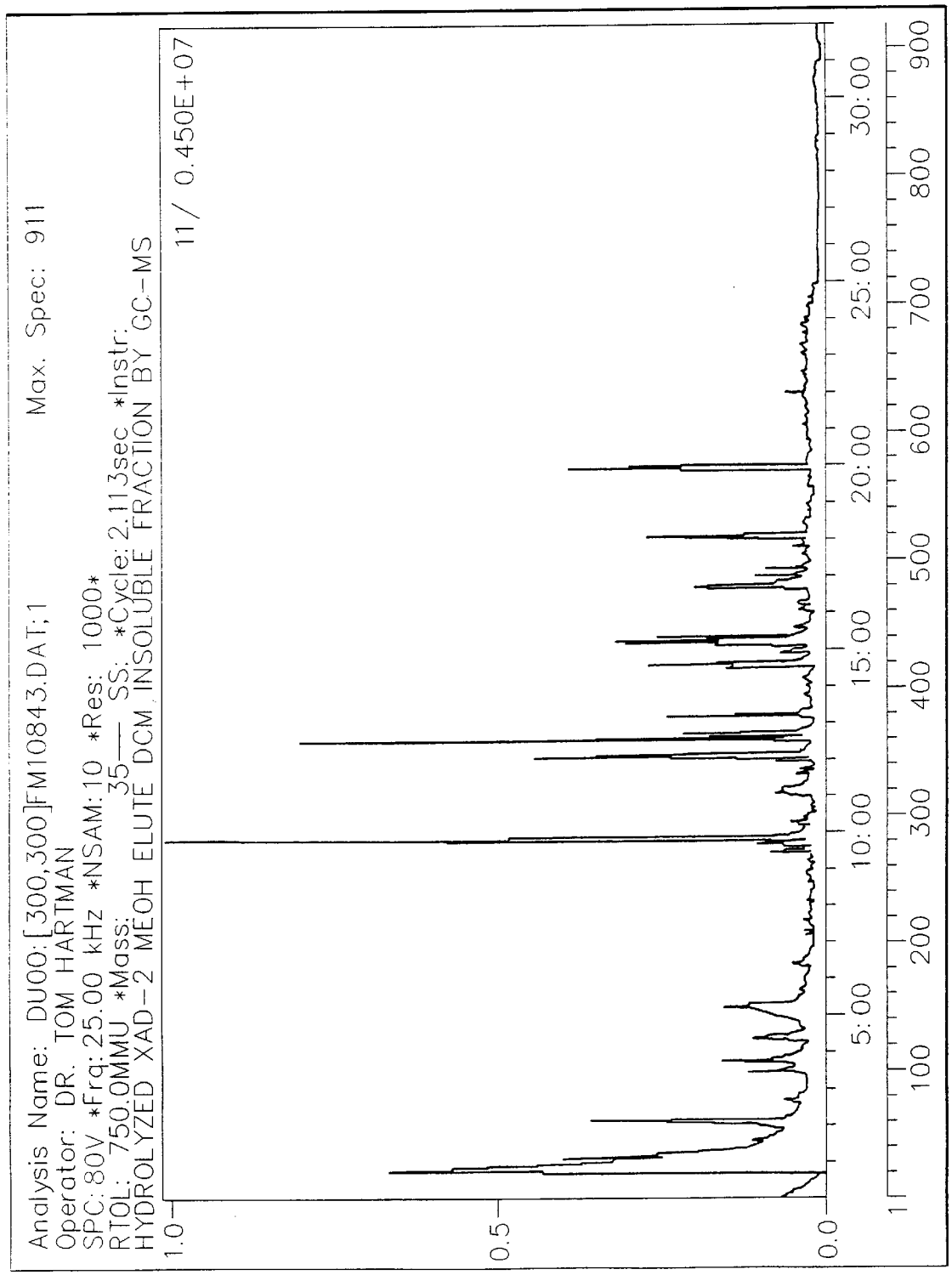
FIGS. 8, 9, and 10 show, respectively, a GC-MS chromatogram, DP data, and LSIMS data for the hydrolyzed XAD-2 resin MeOH eluate DCM-insoluble fraction 29 of FIG. 1.
Figure 9:
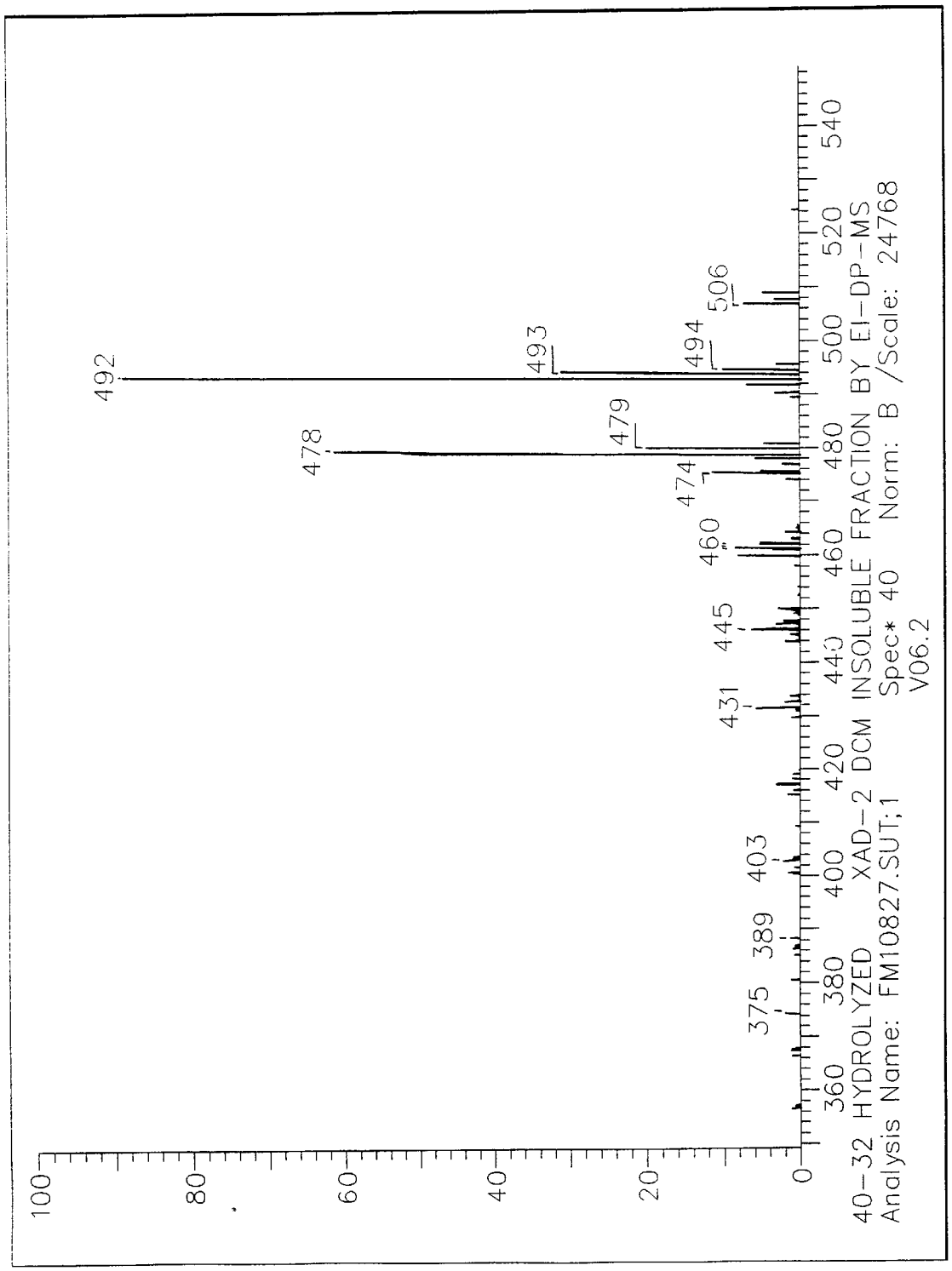
Figure 10:
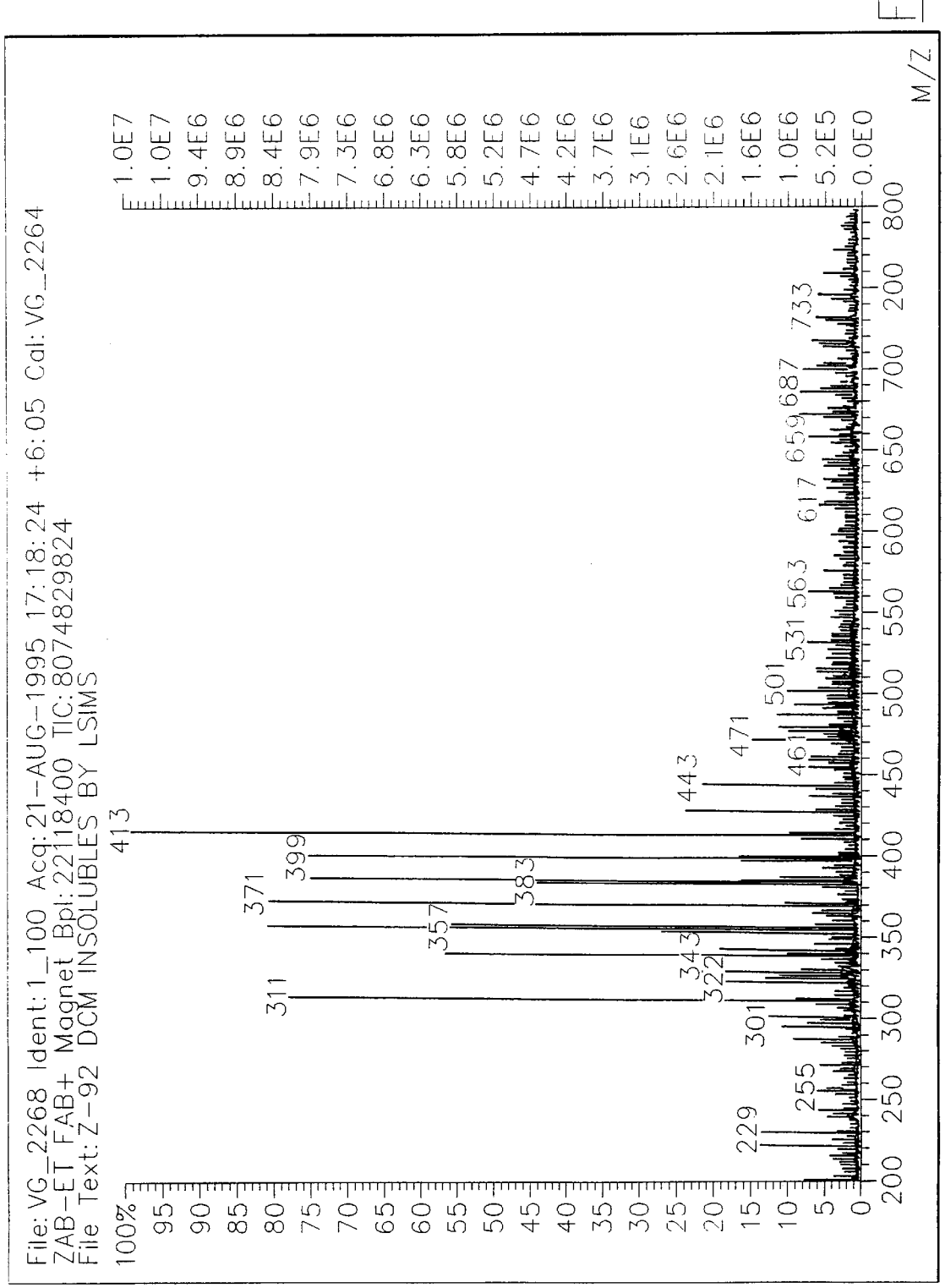

The data on the hydrolyzed XAD-2 resin MeOH eluate DCM-insoluble fraction 29 are summarized in Table 5. The GC-MS chromatogram, DP data, and LSIMS data for this fraction are shown in FIGS. 8, 9, and 10, respectively. Please note that the compounds in Table 3 that appear following hydrolysis are all present as bound components in the original fraction.

TABLE 5

Chemical Composition of Hydrolyzed XAD-2 Resin MeOH Eluate DCM-Insoluble (Fraction 29 of FIG. 1)

| MS Spec # | Compound (Synonyms, Common Names, Comments, Etc.) | CAS # | Peak Area % |
|---|---|---|---|
| 57 | fumaric acid | 110-17-8 | 4.14 |
| 97 | 2-ethyl-1-hexanol (plasticizer degradate) | 104-76-7 | 1.8 |
| 123 | 2-furancarboxylic acid | 88-14-2 | 2.64 |
| 151 | 4-oxo-pentanoic acid (levulinic acid) | 123-76-2 | 5.36 |
| 183 | α-hydroxyhexanoic acid | NA | 0.62 |
| 271 | branched dodecanol isomer | NA | 1.56 |
| 278 | 1-chlorododecane (probably a hydrolysis artifact) | 112-52-7 | 0.91 |
| 282 | 1-dodecanol (lauryl alcohol) | 112-53-8 | 15.7 |
| 318 | dodecanoic acid (lauric acid) | 143-07-7 | 2.54 |
| 345 | tributylphosphate (plasticizer) | 126-73-8 | 1.29 |
| 348 | 1-tetradecanol (myristyl alcohol) | 112-72-1 | 5.89 |
| 361 | 2-ethoxy-1-dodecanol | 29718-44-3 | 7.09 |

TABLE 5-continued

Chemical Composition of Hydrolyzed XAD-2 Resin MeOH Eluate DCM-Insoluble (Fraction 29 of FIG. 1)

| MS Spec # | Compound (Synonyms, Common Names, Comments, Etc.) | CAS # | Peak Area % |
|---|---|---|---|
| 365 | 2,8-dihydroxy-3-methyl-1,4-napthoquinone (Droserone) | NA | 3.29 |
| 378 | tetradecanoic acid (myristic acid) | 544-63-8 | 2.31 |
| 420 | 2-ethoxy-1-tetradecanol | NA | 3.01 |
| 422 | methyl palmitate | 112-39-0 | 0.46 |
| 428 | 7-hydroxy-5-methoxy-2-methyl-4-oxo-4H-1-benzopyran-6-carboxaldehyde | 7338-51-4 | 1.15 |
| 441 | hexadecanoic acid (palmitic acid) | 57-10-3 | 7.54 |
| 440 | α-hydroxylauric acid | NA | 3.4 |
| 461 | heptadecanoic acid (margaric acid) | 506-12-7 | 0.32 |
| 449 | oleic acid | 112-80-1 | 0.69 |
| 480 | linoleic acid | 60-33-3 | 4.93 |
| 511 | α-hydroxymyristic acid | 2507-55-3 | 0.42 |
| 488 | octadecanoic acid (stearic acid) | 57-11-4 | 1.35 |
| 516 | 3-methyl-1,8,9-anthracenetriol (3-methylanthralin, Chrysarobin) | 491-59-8 | 0.42 |
| 520 | 1,8-dihydroxy-3-methyl-9,10-anthracenedione (Chrysophanol, Chrysophanic acid, 1,8-dihydroxy-3-methyl-1,8-anthraquinone) | 481-74-3 | 4.71 |
| 574 | di-2-ethylhexylphthalate (plasticizer) | 117-81-7 | 4.48 |
| DP Data | bis-flavanoids with m.w.'s 478 ($C_{22}H_{22}O_{12}$), 492 ($C_{23}H_{24}O_{12}$) and 506 ($C_{23}H_{22}O_{13}$) exact chemicals structures unknown | NA | 11.98 |

DP = Data is from Electron Ionization Direct Insertion Probe raw data file FM10827

Figure 11:
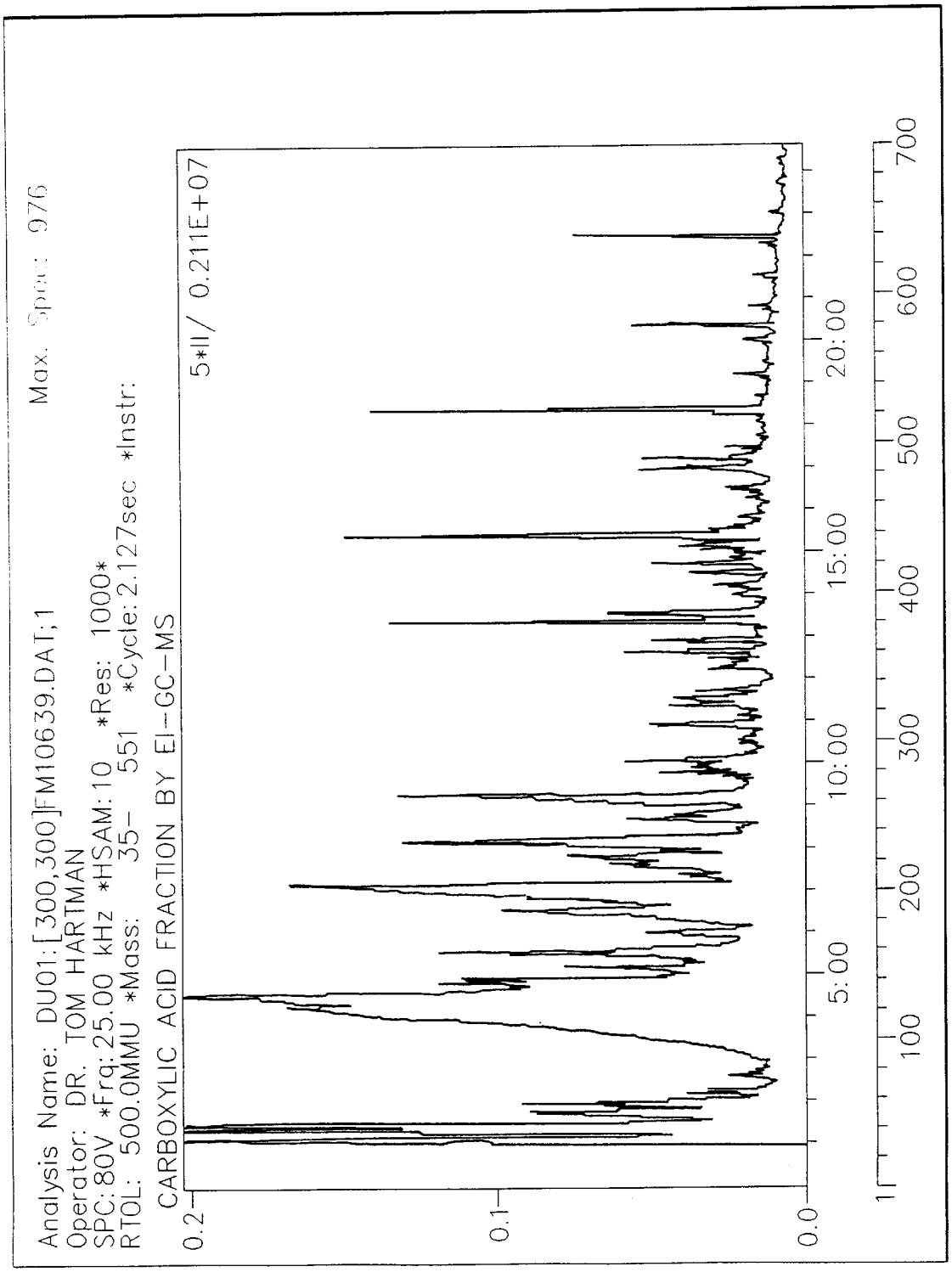
FIGS. 11, 12, and 13 show, respectively, a GC-MS chromatogram, DP data, and LSIMS data for carboxylic acid fraction 28.
Figure 12:
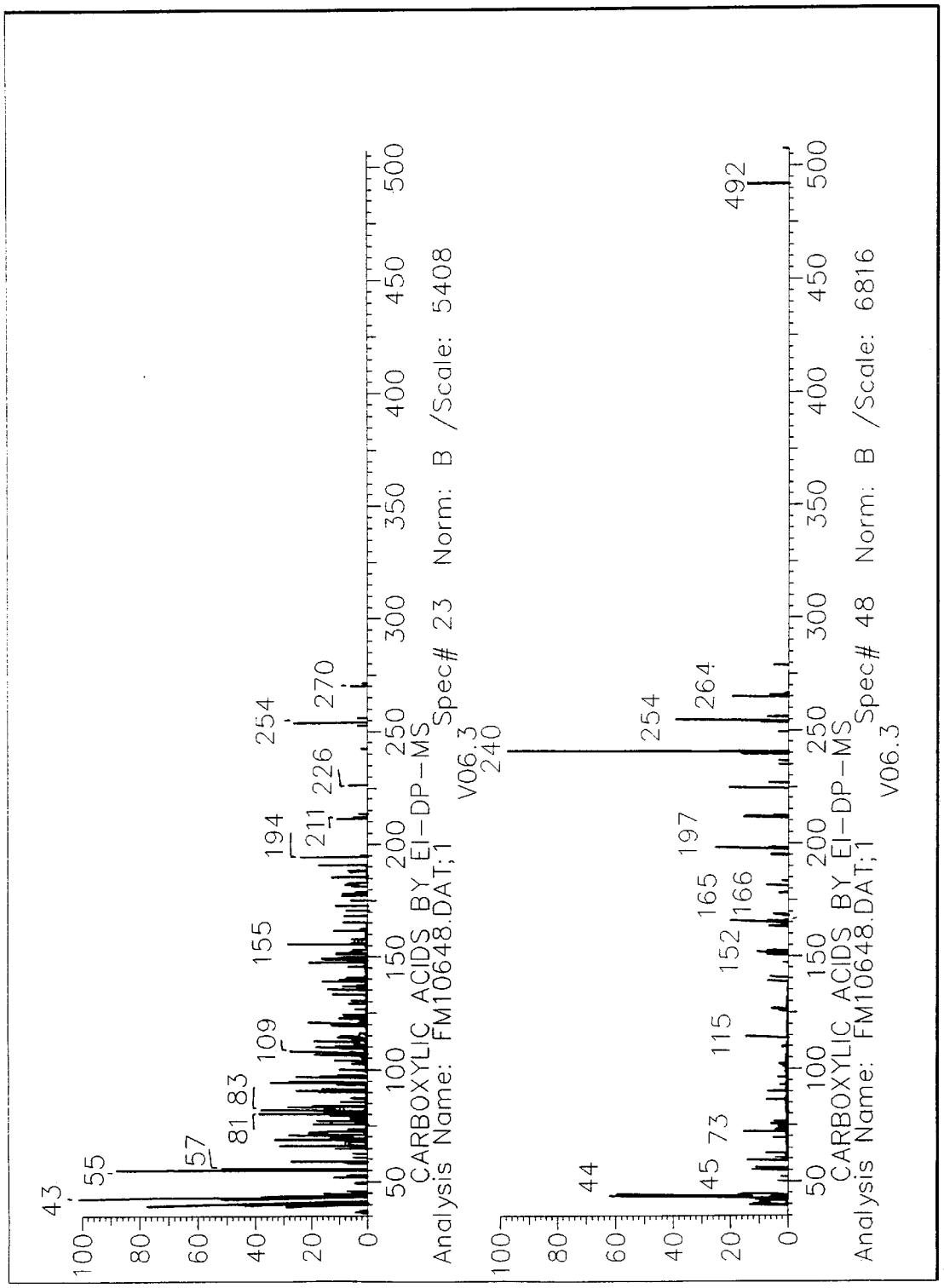
Figure 13:
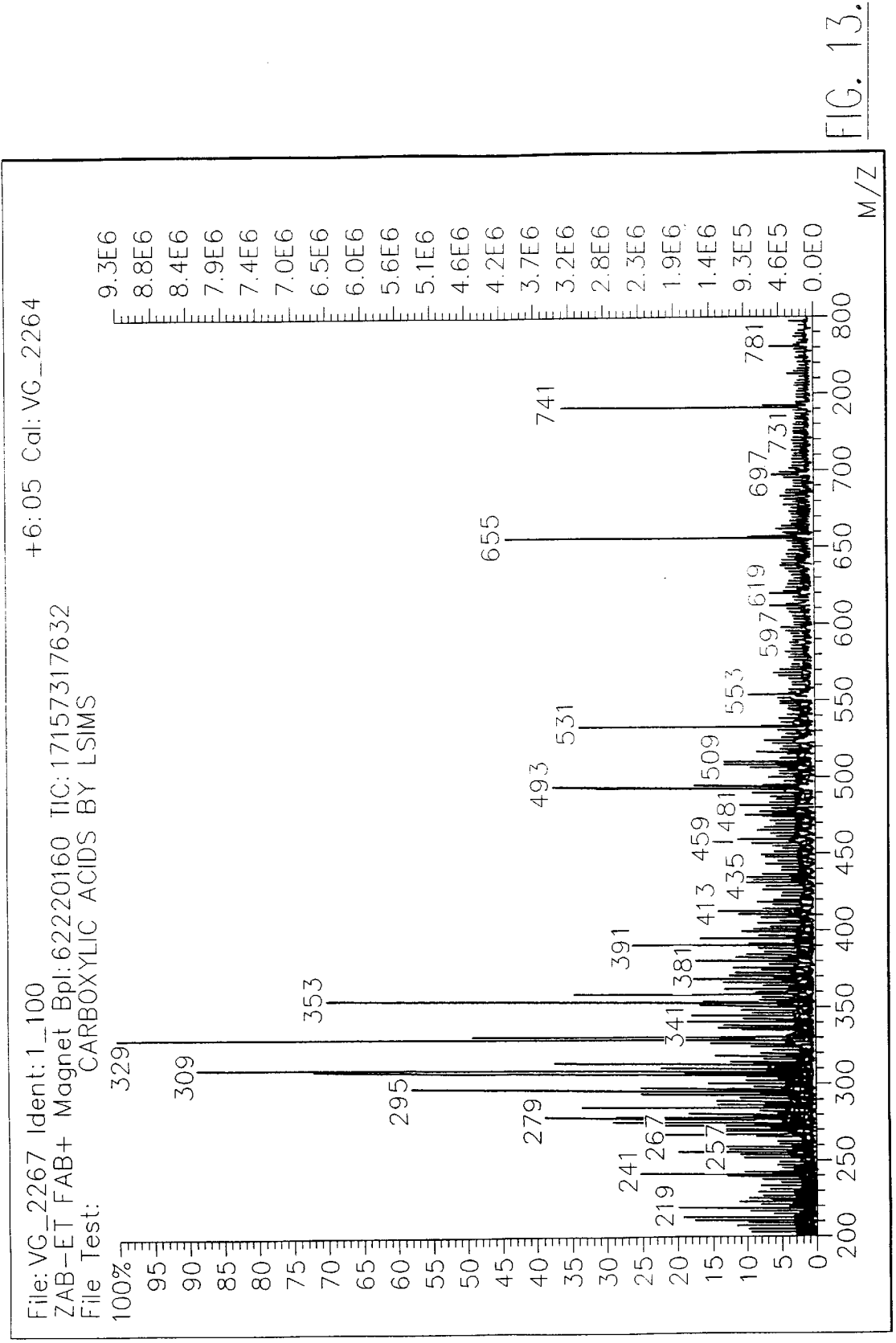

The carboxylic acid fraction 28 data are summarized in Table 6. The GC-MS chromatogram, DP data, and LSIMS data pertaining to this fraction 28 are presented in FIGS. 11, 12, and 13. Carboxylic acid fractions often contain nonvolatile species that do not readily pass through gas chromatography. These compounds can be chemically derivatized into more volatile forms using methylation or silylation reagents. Therefore, the carboxylic acid fraction 28 was methylated using freshly prepared diazomethane reagent. This procedure converts the carboxylic acids into their corresponding methyl esters. Phenols are converted into methyl ethers. The methyl esters and methyl ethers are more volatile and chromatograph better than the free acids.

Figure 14:
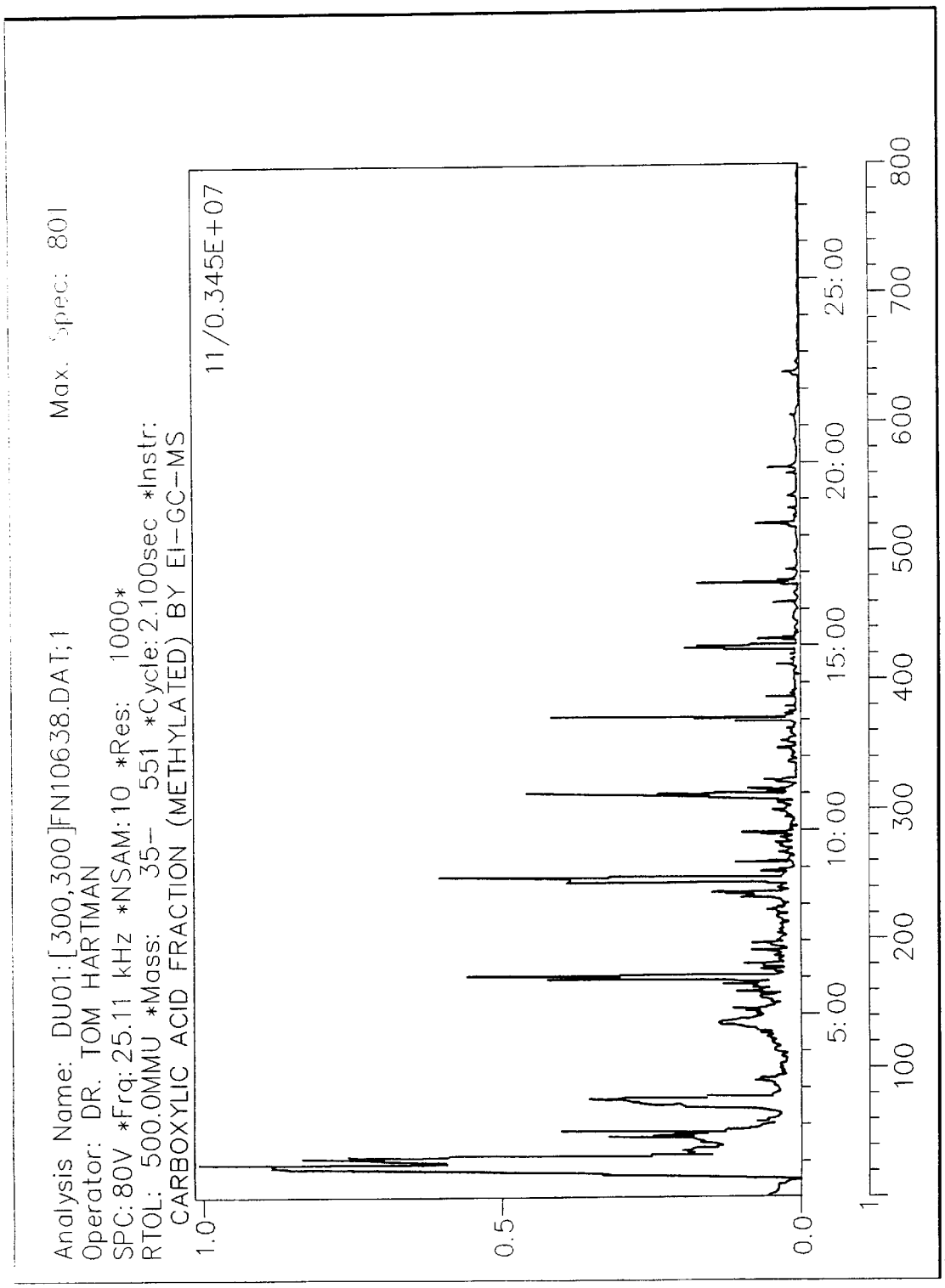
FIG. 14 shows GC-MS chromatogram data from the methylated carboxylic acids of Example 5.

The GC-MS chromatogram from the methylated carboxylic acids is shown in FIG. 14. No additional compounds were detected in the methylated sample. All the same compounds observed in the underivatized carboxylic acid fraction were found as their methylated counterparts.

TABLE 6

Chemical Composition of Carboxylic Fraction (Fraction 28 FIG. 1)

| MS Spec # | Compound (Synonyms, Common Names, Comments, Etc.) | CAS # | Peak Area % |
|---|---|---|---|
| 37–40 | 2-methylacrylic acid | 79-41-4 | 14.4 |
| 49 | 2-methylbutyric acid | 116-53-0 | 2.04 |
| 57 | pentanoic acid | 109-52-4 | 2.2 |
| 118 | hexanoic acid | 142-62-1 | 3.52 |
| 120 | 2-furancarboxylic acid | 88-14-2 | 9.18 |
| 153 | unknown 138 m.w. sulfur containing compound | NA | 2.7 |
| 167 | 2-ethylhexanoic acid | 149-57-5 | 1 |
| 181 | benzoic acid | 65-85-0 | 2.91 |
| 197 | octanoic acid | 124-07-2 | 6.29 |

TABLE 6-continued

Chemical Composition of Carboxylic Fraction
(Fraction 28 FIG. 1)

| MS Spec # | Compound (Synonyms, Common Names, Comments, Etc.) | CAS # | Peak Area % |
|---|---|---|---|
| 217 | benzeneacetic acid | 103-82-2 | 1.2 |
| 227 | nonanoic acid | 112-05-0 | 4.74 |
| 242 | decanoic acid | 334-48-5 | 5.2 |
| 273 | 2-hydroxy-3-methylbenzoic acid (cresotic acid, homosalicylic acid) | 83-40-9 | 0.77 |
| 277 | phenylpropenoic acid (cinnamic acid) | 621-82-9 | 0.69 |
| 305 | 3,4-dichlorobenzoic acid | 51-44-5 | 0.88 |
| 318 | dodecanoic acid (lauric acid) | 143-07-7 | 0.62 |
| 323 | 10-undecenoic acid | 112-38-9 | 0.72 |
| 328 | nonanedioic acid | 123-38-9 | 0.54 |
| 329 | pentachlorophenol (wood preservative) | 87-86-5 | 0.11 |
| 342 | 3-methoxy-4-hydroxybenzaldehyde (vanillin) | 121-33-5 | 0.75 |
| 372 | p-coumaric acid, methyl ester | 3943-97-3 | 1.23 |
| 378 | tetradecanoic acid (myristic acid) | 544-63-8 | 0.72 |
| 395 | methyl ferulate | 2309-07-1 | 0.72 |
| 408 | methyl ester of 3,4-dimethoxycinnamic acid | 5396-64-5 | 0.71 |
| 414 | 1,4-benzene dicarboxylic acid (terephthalic acid) | 100-21-0 | 0.67 |
| 423 | 3,4-dihydro-4,8-dihydroxy-3-methyl-isocoumarin (6-hydroxymellein) | 309-51-112 | 0.42 |
| 427 | 9-hexadecenoic acid (palmitoleic acid) | 2091-29-4 | 0.55 |
| 434 | hexadecanoic acid (palmitic acid) | 57-10-3 | 1.9 |
| 438 | 9-octadecenoic acid (oleic acid) | 112-80-1 | 0.49 |
| 478 | 9,12-octadecadienoic acid (linoleic acid) | 60-33-3 | 1.03 |
| 484 | octadecanoic acid (stearic acid) | 57-11-4 | 0.69 |
| 491 | 3-methyl-1,8,9-anthracenetriol (3-methylanthralin, Chrysarobin) | 491-59-8 | 0.55 |
| 516 | 1,8-dihydroxy-3-methyl-9,10-anthracenedione (Chrysophanol, Chrysophanic acid, 1,8-dihydroxy-3-methyl-1,8-anthraquinone) | 481-74-3 | 1.3 |
| 572 | di-2-ethylhexylphthalate (plasticizer) | 117-81-7 | 0.6 |
| 633 | squalene | 7683-64-9 | 0.74 |
| DP Data | bis-flavanoids with m.w.'s 492 ($C_{23}H_{24}O_{12}$) and 506 ($C_{23}H_{22}O_{13}$) exact chemicals structures unknown | NA | 27.22 est. total for DP & LSIMS |
| LSIMS Data | unknown high mass compounds m.w. 530, 654 and 740 | NA | 27.22 est. total for DP & LSIMS |

DP = Data is from Electron Ionization Direct Insertion Probe raw data file FM10648
LSIMS = Liquid Secondary Ion Mass Spectrometry Data file VG2267

Figure 15:
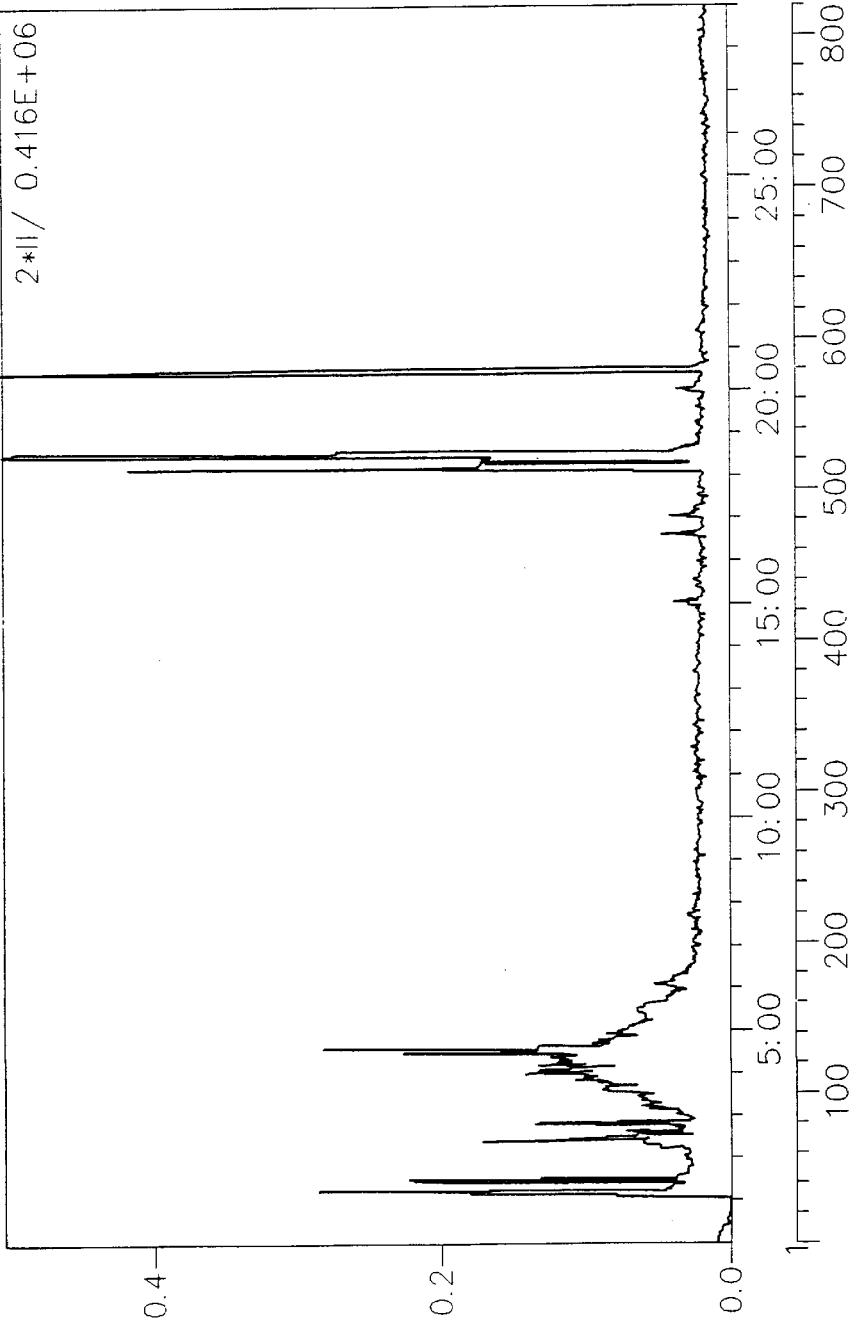
FIGS. 15, 16, and 17 show, respectively, a GC-MS chromatogram, DP data, and LSIMS data for the neutral/phenol fraction 36 of FIG. 1.
Figure 16:
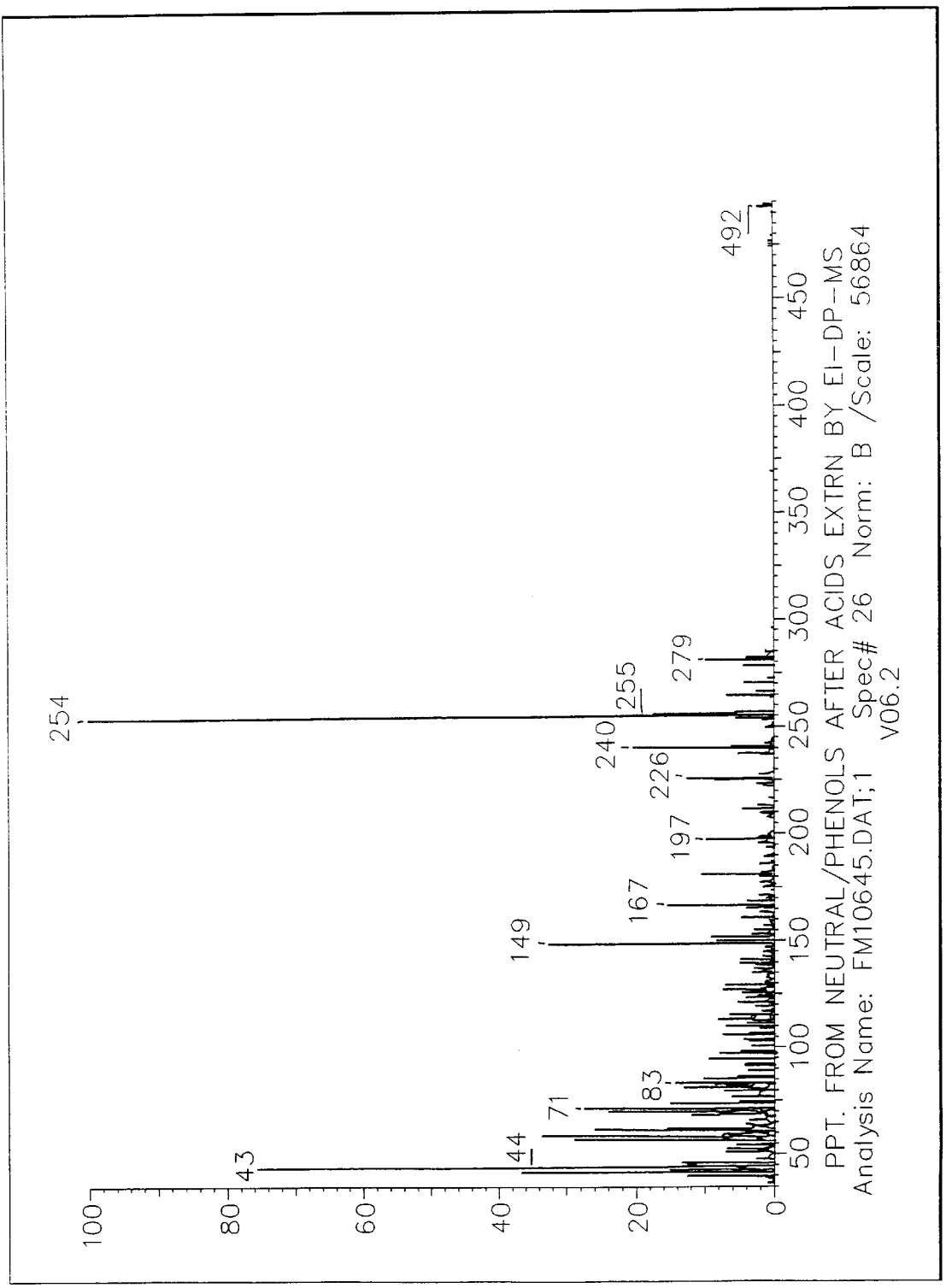
Figure 17:
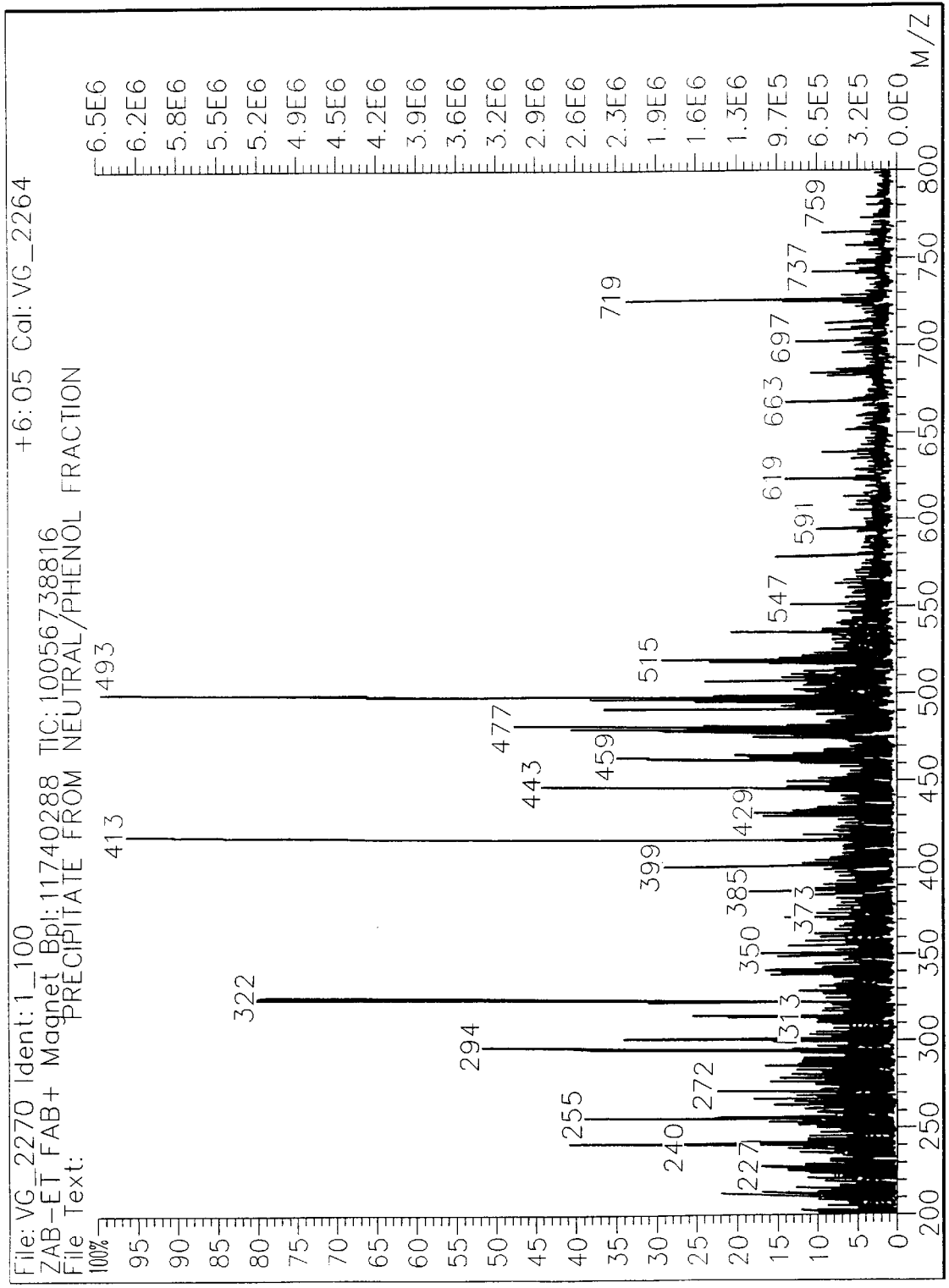
Figure 18:
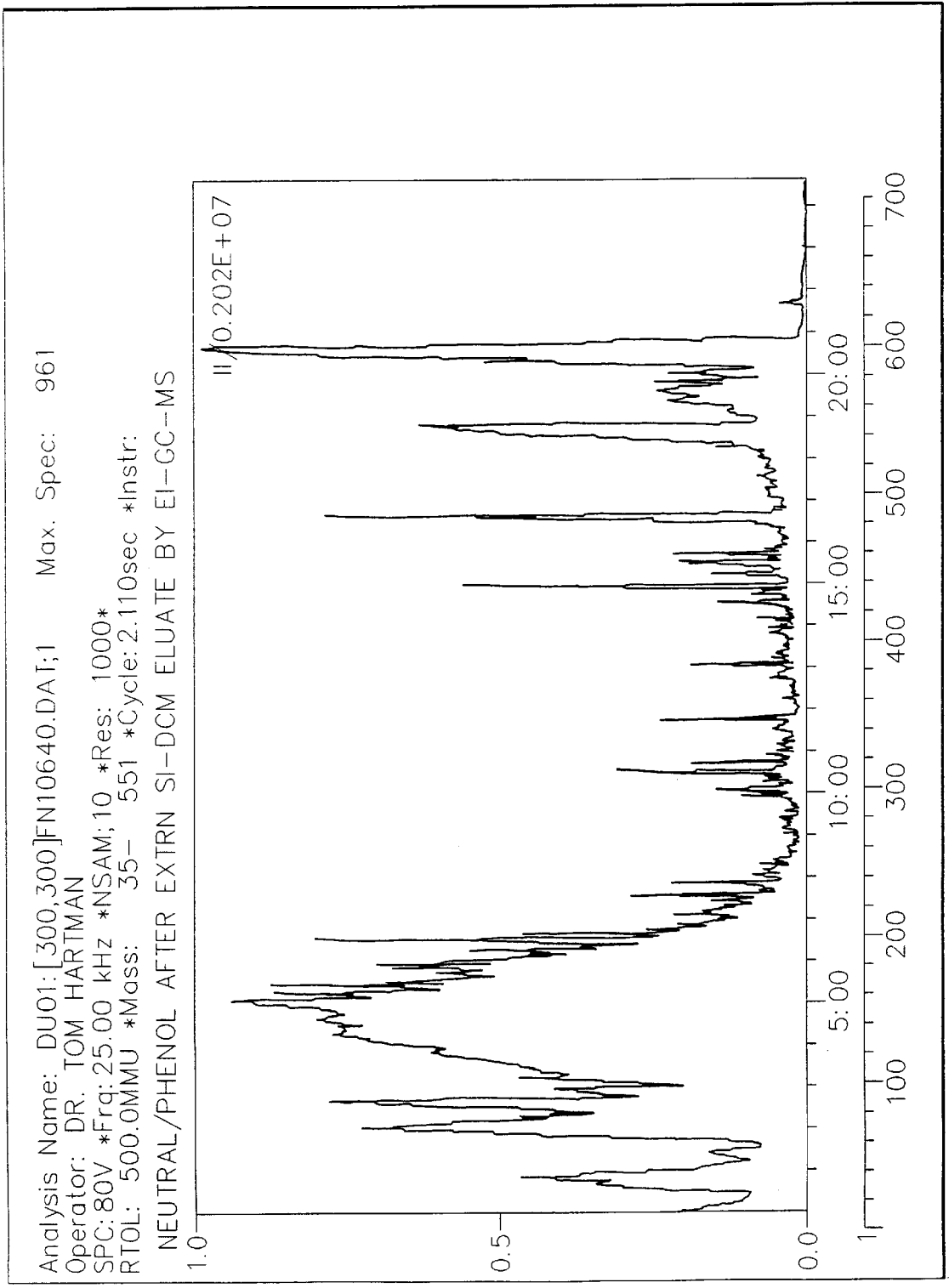
FIGS. 18–23 show, respectively, GC-MS chromatograms, DP data, and LSIMS data for the neutral/phenol fraction DCM silica gel eluate and the neutral/phenol fraction MeOH silica gel eluate.
Figure 19:
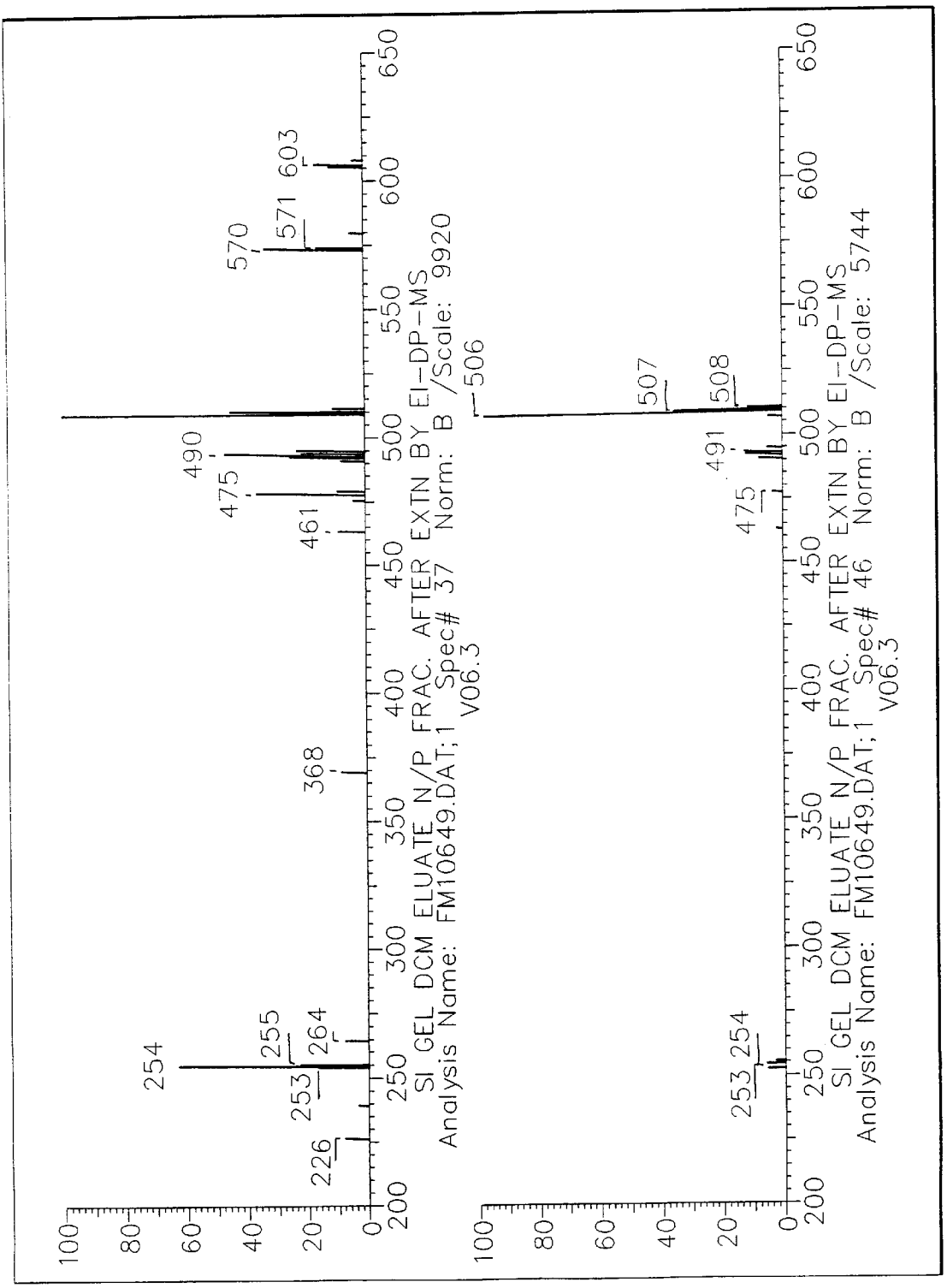
Figure 20:
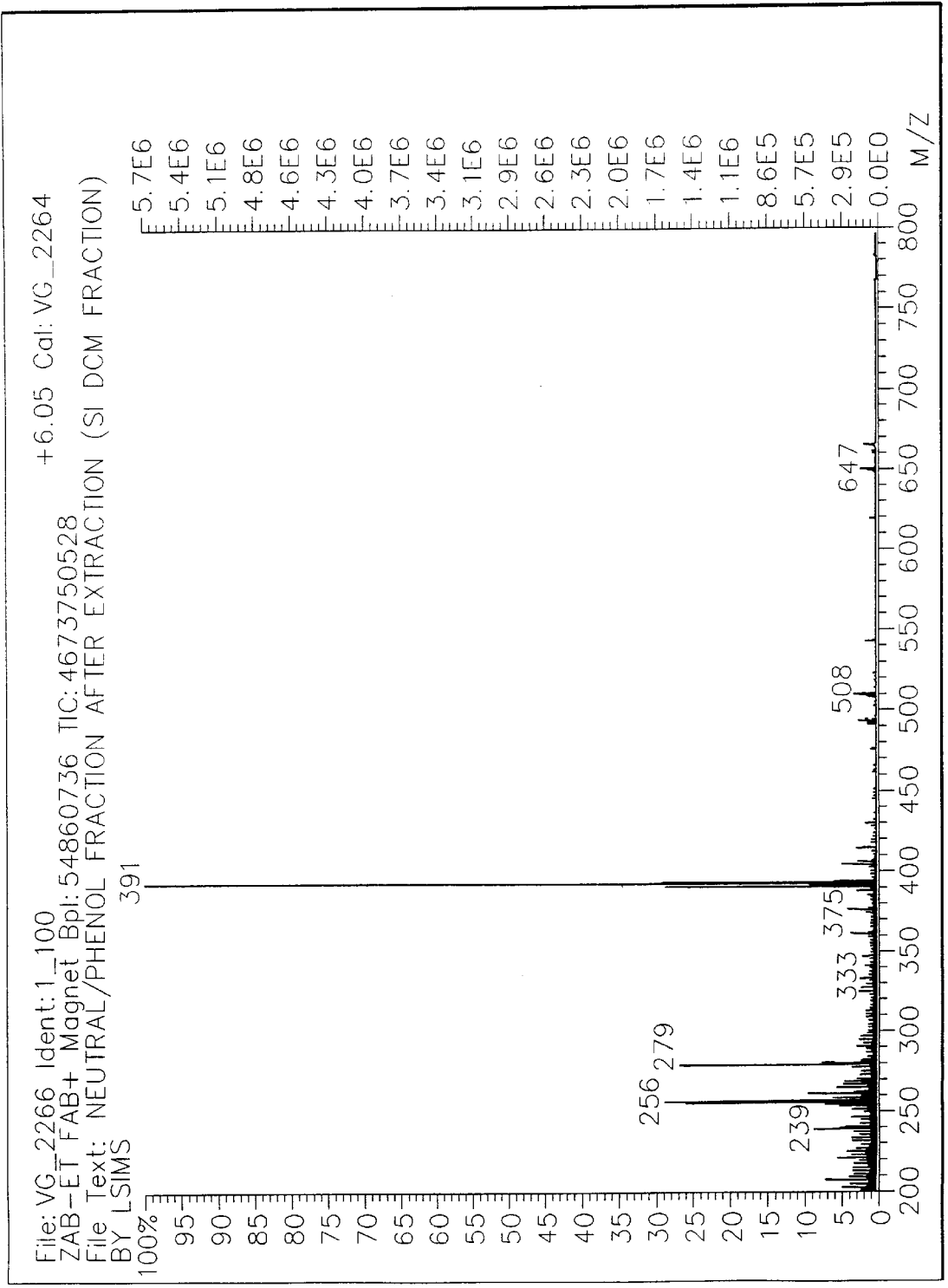
Figure 21:
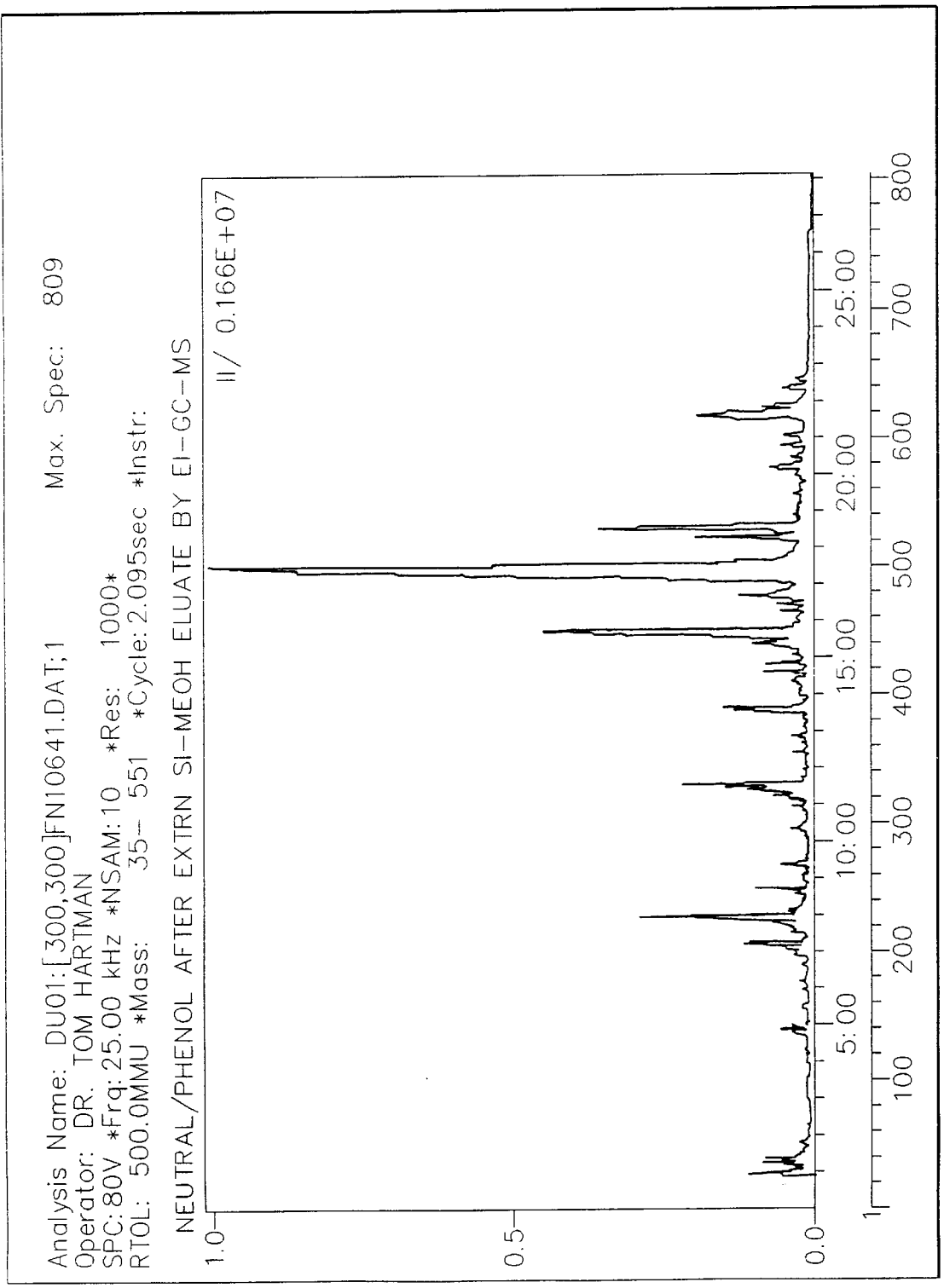
Figure 22:
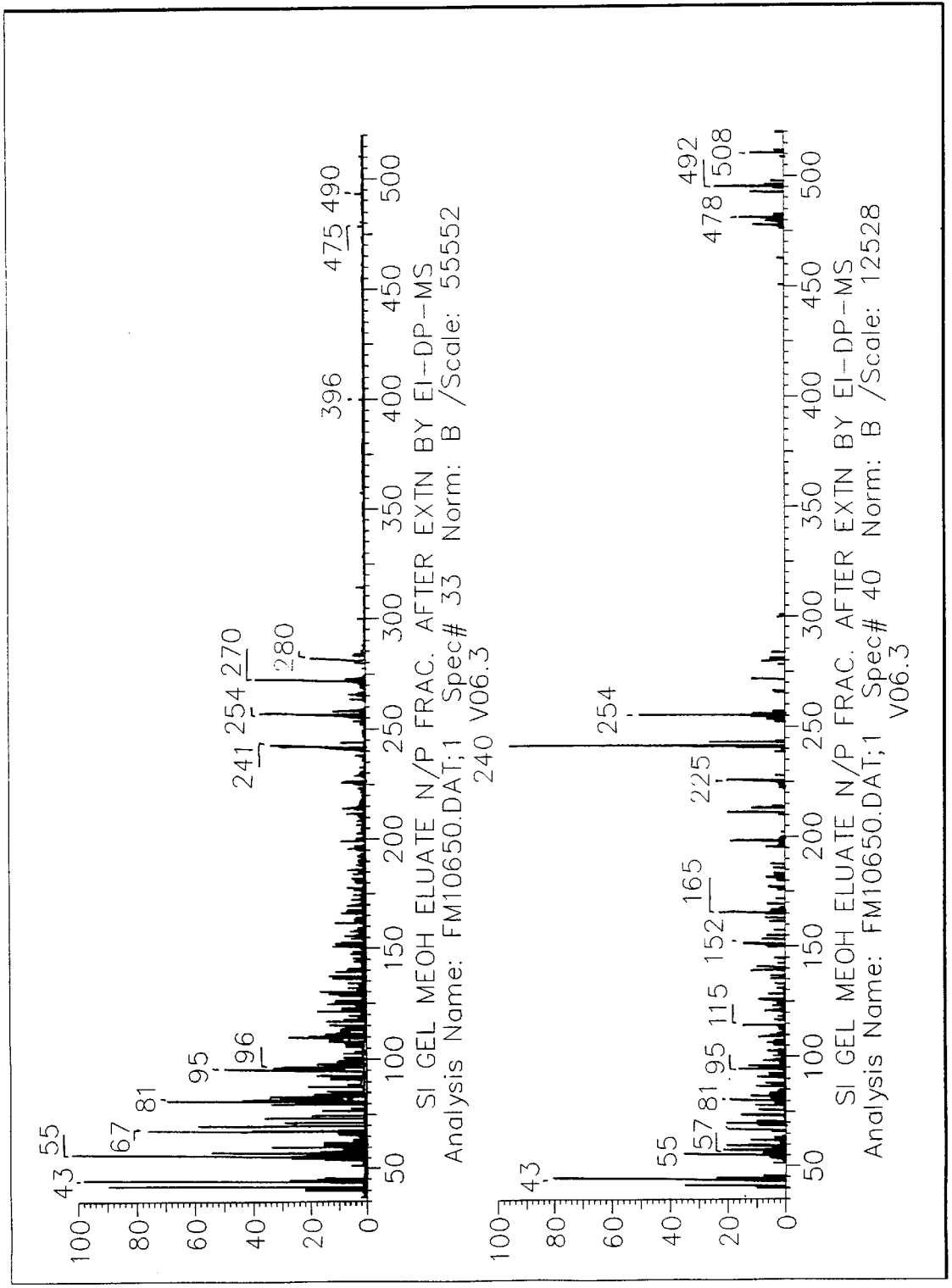
Figure 23:
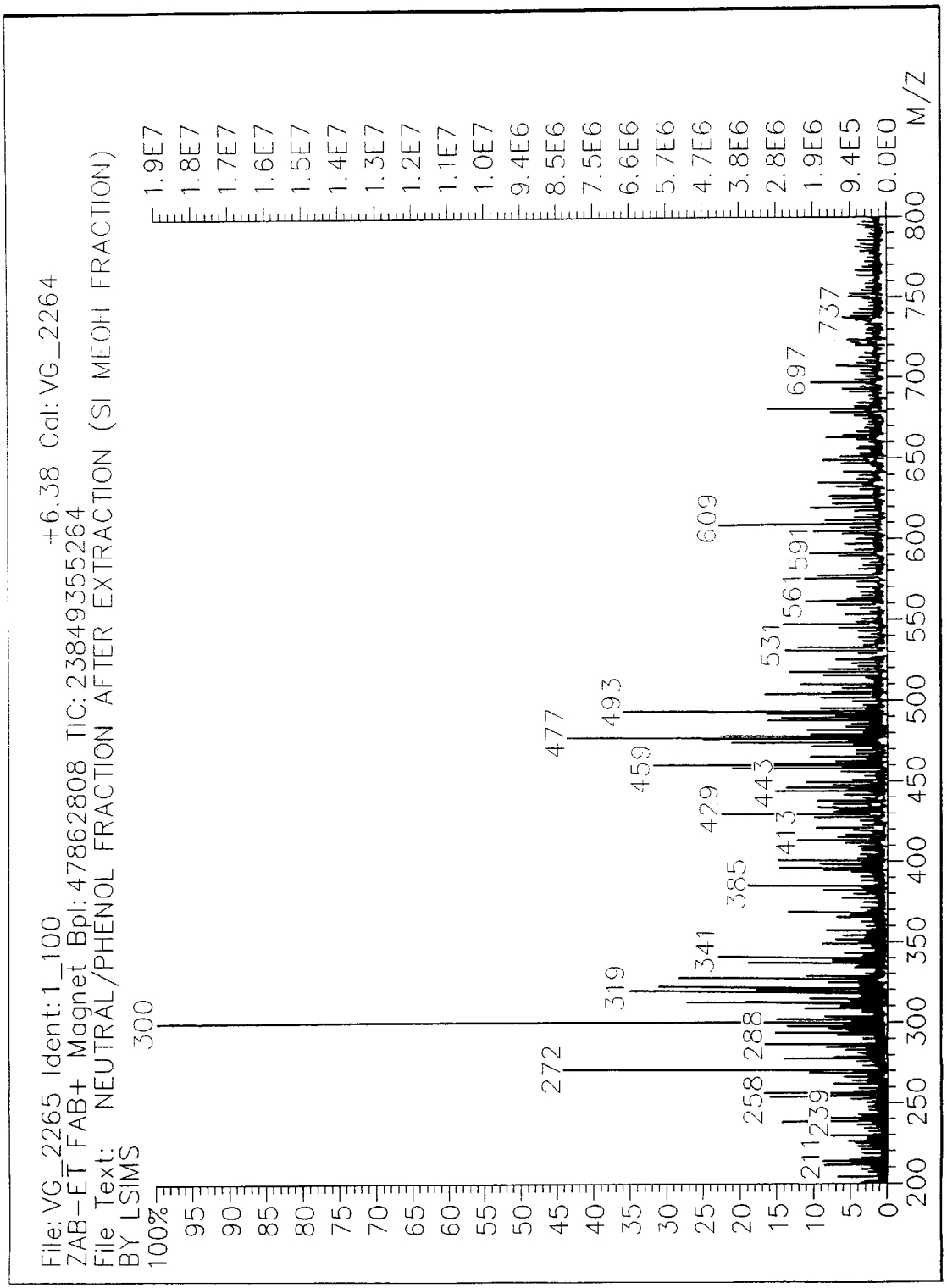

Table 7 summarizes the chemical composition of the yellow precipitate which was isolated from the neutral/phenol fraction 36 after extraction of the carboxylic acids. This fraction, which contains relatively few components, possesses the highest degree of activity in the cell culture bioassay. The GC-MS chromatogram, DP data, and LSIMS data pertaining to this fraction are shown in FIGS. 15–17.

TABLE 7

Chemical Composition Precipitate Neutral/Phenol
Fraction after Extraction of Acids (Fraction 36 of FIG. 1)

| MS Spec # | Compound (Synonyms, Common Names, Comments, Etc.) | CAS # | Peak Area % |
|---|---|---|---|
| 419 | methyl palmitate | 112-39-0 | 0.53 |
| 464 | methyl linoleate | 112-63-0 | 1.09 |
| 510 | 3-methyl-1,8,9-anthracenetriol (3-methylanthralin, Chrysarobin) | 491-59-8 | 19.69 |
| 517 | 1,8-dihydroxy-3-methyl-9,10-anthracenedione (Chrysophanol, Chrysophanic acid, 1,8-dihydroxy-3-methyl-1,8-anthraquinone) | 481-74-3 | 57.41 |
| 583 | di-2-ethylhexylphthalate (plasticizer) | 117-81-7 | 18.35 |
| DP Data | bis-flavanoids with m.w.'s 474 ($C_{23}H_{22}O_{11}$), 492 ($C_{23}H_{24}O_{12}$), 506 ($C_{23}H_{22}O_{13}$) and 508 ($C_{23}H_{24}O_{13}$) exact chemicals structures unknown | NA | 2.93 (est. total for DP & LSIMS) |
| LSIMS Data | unknown high mass compounds m.w. 618, 662, 696, 718, 736 and 758 | NA | 2.93 (est. total for DP & LSIMS data |

DP = Data is from Electron Ionization Direct Insertion Probe raw data file FM10645
LSIMS = Liquid Secondary Ion Mass Spectrometry Data file VG2270

The neutral/phenol fraction following extraction of carboxylic acids and harvesting of the yellow precipitate was still too complex for direct analysis. Therefore, it was subjected to additional fractionation using a silica gel solid phase extraction minicolumn procedure. The fraction was passed through the silica gel column and was washed with DCM. A second more polar fraction was then eluted from the column using methanol. Out of the original 1.32 g of neutral/phenol fraction were recovered 0.73 g (0.15% of original crude extract) in the DCM eluate and 0.59 g (0.12%) in the MeOH eluate. Therefore, the neutral/phenol fraction following extraction of carboxylic acids and harvesting of yellow precipitate was split into two additional subfractions for analysis. These were named the neutral/phenol fraction DCM silica gel eluate and the neutral/phenol fraction MEOH silica gel eluate. The chemical compositions of these two fractions are summarized in Tables 8 and 9. The GC-MS chromatograms, DP data, and LSIMS data pertaining to these two fractions are shown in FIGS. 17 through 22.

TABLE 8

Chemical Composition Neutral/Phenol
Fraction Silica Gel MEOH Eluate

| MS Spec # | Compound (Synonyms, Common Names, Comments, Etc.) | CAS # | Peak Area % |
|---|---|---|---|
| 134 | 3,5,5-trimethyl-2-cyclohexene-1-one (isophorone) | 78-59-1 | 0.83 |
| 205–225 | 5-hydroxymethylfurfuryl acetate (HMF acetate) | 10551-58-3 | 6.24 |
| 231 | glycerylmonoacetate | 26446-35-5 | 1.03 |
| 244 | glyceryldiacetate | 25395-31-7 | 0.6 |
| 246 | glyceryltriacetate (triacetin) | 102-76-1 | 1 |
| 254 | decanoic acid | 334-48-5 | 0.18 |
| 295 | 1,4-butanediol diacetate | 628-67-1 | 0.57 |
| 311 | unknown aromatic acetate | NA | 0.53 |
| 319 | unknown aromatic acetate | NA | 0.65 |
| 326 | dodecanoic acid (lauric acid) | 143-07-7 | 2.11 |
| 334 | 1,4-benzenediol monoacetate (hydroquinone monoacetate) | NA | 2.03 |
| 353 | unknown aromatic acetate | NA | 0.29 |
| 359 | unknown aromatic acetate | NA | 0.13 |

TABLE 8-continued

Chemical Composition Neutral/Phenol Fraction Silica Gel MEOH Eluate

| MS Spec # | Compound (Synonyms, Common Names, Comments, Etc.) | CAS # | Peak Area % |
|---|---|---|---|
| 372 | myristic acid | 544-63-8 | 2.66 |
| 399 | unknown aromatic acetate | NA | 0.5 |
| 405 | pentadecanoic acid | 1002-84-2 | 1.6 |
| 421 | 1,4-benzenedicarboxylic acid (terephthalic acid) | 100-21-0 | 0.58 |
| 428 | hexadecanoic acid (palmitic acid) | 57-10-3 | 11.58 |
| 456 | heptadecanoic acid | 506-12-7 | 1.67 |
| 474 | linoleic acid | 60-33-3 | 2.88 |
| 500 | octadecanoic acid (stearic acid) | 57-11-4 | 39.02 |
| 520 | 3-methyl-1,8,9-anthracenetriol (3-methylanthralin, Chrysarobin) | 491-59-8 | 2.57 |
| 529 | 1,8-dihydroxy-3-methyl-9,10-anthracenedione (Chrysophanol, Chrysophanic acid, 1,8-dihydroxy-3-methyl-1,8-anthraquinone) | 481-74-3 | 5.7 |
| 539–575 | mixture of long chain aliphatic acetates | NA | 4 |
| 583 | di-2-ethylhexylphthalate (plasticizer) | 117-81-7 | 0.55 |
| 616 | 1,8-dihydroxy-3-(hydroxymethyl)-9,10-anthracenedione (Aloe-Emodin) | NA | 3.82 |
| 622 | monoacetate derivative of 1,8-dihydroxy-3-(hydroxymethyl)-9,10-anthracenedione (Aloe-Emodin monoacetate) | NA | 1.34 |
| 636 | unknown 378 m.w. aromatic acetate | NA | 0.77 |
| 644 | squalene | 7683-64-9 | 0.27 |
| DP Data | bis-flavanoids with m.w.'s 474 ($C_{23}H_{22}O_{11}$), 478 ($C_{22}H_{22}O_{12}$), 490 ($C_{23}H_{22}O_{12}$), 492 ($C_{23}H_{24}O_{12}$), 506 ($C_{23}H_{22}O_{13}$) and 508 ($C_{23}H_{24}O_{13}$) exact chemicals structures unknown | NA | 4.3 (est. total for DP & LSIMS) |
| LSIMS Data | unknown high mass compounds m.w. 608, 680 and 696 | NA | 4.3 (est. total for DP & LSIMS data) |

DP = Data is from Electron Ionization Direct Insertion Probe raw data file FM10650
LSIMS = Liquid Secondary Ion Mass Spectrometry Data file VG2265

TABLE 9

Chemical Composition Neutral/Phenol Fraction Silica Gel DCM Eluate

| MS Spec # | Compound (Synonyms, Common Names, Comments, Etc.) | CAS # | Peak Area % |
|---|---|---|---|
| 263 | unknown 154 m.w. compound | NA | 0.29 |
| 268 | 2,3-dihydro-2,5-dimethyl-4H-1-benzopyran-4-one | 69687-87-2 | 0.88 |
| 278 | S-6 hexasulfide (six membered ring structure) | NA | 1.35 |
| 283 | 2,6-di-t-butyl-p-hydroxyanisole (antioxidant) | NA | 2.12 |
| 295 | butylated hydroxy toluene (BHT, antioxidant) | 128-37-0 | 3.65 |
| 301 | methyl laurate | 111-82-0 | 1.47 |
| 323 | diethylphthalate (plasticizer) | 84-66-2 | 1.06 |
| 329 | dodecyl acetate | 112-66-3 | 1.82 |
| 358 | unknown benzoate | NA | 0.65 |
| 365 | methyl tridecanoate | 1731-88-0 | 1.35 |
| 369 | α-hexylcinnamic aldehyde | 101-86-0 | 0.65 |
| 373 | benzyl benzoate | 120-51-4 | 0.71 |
| 386 | methylpentadecanoate | 7132-64-1 | 0.82 |
| 390 | tetradecyl acetate | 638-59-5 | 0.59 |

TABLE 9-continued

Chemical Composition Neutral/Phenol Fraction Silica Gel DCM Eluate

| MS Spec # | Compound (Synonyms, Common Names, Comments, Etc.) | CAS # | Peak Area % |
|---|---|---|---|
| 404 | benzyl salicylate | 118-58-1 | 1.35 |
| 417 | acetylferulic acid | 2596-47-6 | 2.12 |
| 425 | methyl palmitate | 112-39-0 | 4.53 |
| 433 | dibutylphthalate | 84-74-2 | 2.00 |
| 441 | sulfur (S-8, cyclic sulfur, ortho-thrombic sulfur, molecular sulfur) | 10544-50-0 | 3.59 |
| 447 | hexadecyl acetate | 629-70-9 | 1.88 |
| 451 | methyl heptadecanoate | 1731-92-6 | 0.94 |
| 471 | methyl linoleate | 112-63-0 | 15.82 |
| 478 | methyl stearate | 112-61-8 | 0.76 |
| 515 | 3-methyl-1,8,9-anthracenetriol (3-methylanthralin, Chrysarobin) | 491-59-8 | 5.06 |
| 519–533 | 1,8-dihydroxy-3-methyl-9,10-anthracenedione (Chrysophanol, Chrysophanic acid, 1,8-dihydroxy-3-methyl-1,8-anthraquinone) | 481-74-3 | 15.00 |
| 543 | di-2-ethylhexylphthalate (plasticizer) | 117-81-7 | 12.53 |
| 617 | monoacetate derivative of 1,8-dihydroxy-3-(hydroxymethyl)-9,10-anthracenedione (Aloe-Emodin monoacetate) | NA | 6.24 |
| 639 | methyl farnesate | 10485-70-8 | 1.06 |
| DP Data | bis-flavanoids with m.w.'s 474 ($C_{23}H_{22}O_{11}$), 490 ($C_{23}H_{22}O_{12}$), 492 ($C_{23}H_{24}O_{12}$), 506 ($C_{23}H_{22}O_{13}$) and 508 ($C_{23}H_{24}O_{13}$) exact chemicals structures unknown, also unknown peaks at m.w. 570 and 602 | NA | 9.71 (est. total for DP & LSIMS) |
| LSIMS Data | unknown high mass compounds m.w. 540, 616, 646 and 662 | NA | 9.71 (est. total for DP & LSIMS data) |

DP = Data is from Electron Ionization Direct Insertion Probe raw data file FM10649
LSIMS = Liquid Secondary Ion Mass Spectrometry Data file VG2266

The data obtained from all of the fractions of Example 4 were pooled together and normalized to produce a comprehensive summary. These data are summarized in Tables 10A–F, which describe the chemical composition of the organic soluble fraction, which constitutes approximately 1% of the treatment solution on a w/w basis but contains 100% of the biological activity. The compounds in this table are grouped together by chemical class. It should be noted that the quantitative date (% w/w) provided in this and the other tables are not exact but rather are semiquantitative. The data were derived from a combination of GC area % integrations and from gravimetric determinations made throughout the fractionation. Highly accurate quantitation data would only be possible if analytical reference standards were available for all compounds detected so that detector response factors could be determined and the data adjusted.

TABLE 10A

Data Summary: Composition of Organic Soluble Fraction Grouped by Chemical Class

| Aliphatic Carboxylic Acids | CAS # | % w/w |
|---|---|---|
| 2-methylacrylic acid | 79-41-4 | 0.27 |
| 2-methylbutyric acid | 116-53-0 | 0.04 |
| fumaric acid | 110-17-8 | 1.50 |
| pentanoic acid | 109-52-4 | 0.04 |

TABLE 10A-continued

Data Summary: Composition of Organic Soluble Fraction Grouped by Chemical Class

| Aliphatic Carboxylic Acids | CAS # | % w/w |
|---|---|---|
| hexanoic acid | 142-62-1 | 0.07 |
| 2-furancarboxylic acid | 88-14-2 | 1.13 |
| 2-ethylhexanoic acid | 149-57-5 | 0.02 |
| 4-oxo-pentanoic acid (levulinic acid) | 123-76-2 | 1.94 |
| α-hydroxyhexanoic acid | NA | 0.23 |
| octanoic acid | 124-07-2 | 0.118 |
| nonanoic acid | 112-05-0 | 0.09 |
| decanoic acid | 334-48-5 | 0.11 |
| dodecanoic acid (lauric acid) | 143-07-7 | 1.09 |
| 10-undecenoic acid | 112-38-9 | 0.01 |
| nonanedioic acid | 123-38-9 | 0.01 |
| tetradecanoic acid (myristic acid) | 544-63-8 | 1.05 |
| pentadecanoic acid | 1002084-2 | 0.12 |
| hexadecanoic acid (palmitic acid) | 57-10-3 | 9.82 |
| α-hydroxylauric acid | NA | 1.232 |
| α-hydroxymyristic acid | 2507-55-3 | 0.15 |
| heptadecanoic acid | 506-12-7 | 0.24 |
| oleic acid | 112-80-1 | 0.259 |
| linoleic acid | 60-33-3 | 12.26 |
| stearic acid | 57-11-4 | 3.43 |
| palmitoleic acid | 2091-29-4 | 0.01 |

TABLE 10B

| Aromatic Carboxylic Acids | | |
|---|---|---|
| benzoic acid | 65-85-0 | 0.06 |
| benzeneacetic acid | 103-82-2 | 0.02 |
| 3,4-dichlorobenzoic acid | 51-44-5 | 0.02 |
| 1,4-benzenedicarboxylic acid (terephthalic acid) | 100-21-0 | 0.06 |
| cinnamic acid | 621-82-9 | 0.01 |
| acetyl ferulic acid | 2596-47-6 | 0.20 |

TABLE 10C

| Esters | | |
|---|---|---|
| glyceryl monoacetate | 26446-35-5 | 0.08 |
| glyceryl diacetate | 25395-31-7 | 0.04 |
| glyceryl triacetate (triacetin) | 102-76-1 | 0.08 |
| 1,4-butanediol diacetate | 628-67-1 | 0.04 |
| 2-hydroxy-5-methylfurfuryl acetate (HMF acetate) | 10551-58-3 | 0.47 |
| diethylphthalate (plasticizer) | 84-66-2 | 0.10 |
| dibutylphthalate (plasticizer) | 84-74-2 | 0.21 |
| di-2-ethylhexylphthalate (plasticizer) | 117-81-7 | 11.70 |
| tributylphosphate (plasticizer) | 126-73-8 | 0.47 |
| methyl laurate | 111-82-0 | 0.14 |
| methyl tridecanoate | 1731-88-0 | 0.13 |
| methyl pentadecanoate | 7132-64-1 | 0.08 |
| methyl palmitate | 112-39-0 | 0.60 |
| methyl heptadecanoate | 1731-92-6 | 0.09 |
| methyl linoleate | 112-63-0 | 1.51 |
| methyl stearate | 112-61-8 | 0.07 |
| methyl farnesate | 10485-70-8 | 0.10 |
| dodecyl acetate | 112-66-3 | 0.17 |
| tetradecyl acetate | 638-59-5 | 0.06 |
| hexadecyl acetate | 629-70-9 | 0.18 |
| benzyl benzoate | 120-51-4 | 0.54 |
| benzyl salicylate | 118-58-1 | 0.13 |
| methyl ester of 3,4-dimethoxy cinnamic acid | 5396-64-5 | 0.01 |
| unknown aromatic acetates | NA | 0.16 |
| mixture of long chain aliphatic acetates | NA | 0.30 |
| unknown benzoate | NA | 0.06 |
| unknown 378 m.w. aromatic acetate | NA | 0.06 |

TABLE 10D

| Phenolic Compounds | | |
|---|---|---|
| phenol | 108-95-2 | 0.09 |
| 2-hydroxy-3-methylbenzoic acid (cresotic acid, homosalicylic acid) | 83-40-9 | 0.01 |
| ferulic acid methyl ester | 2309-07-1 | 0.01 |
| benzyl salicylate | 118-58-1 | 0.13 |
| 3,4-dihydro-4,8-dihydroxy-3-methylisocoumarin (6-hydroxymellein) | 309-51-112 | 0.01 |
| 7-hydroxy-5-methoxy-2-methyl-4-oxo-4H-1-benzopyran-6-carboxaldehyde | 7338-51-4 | 0.42 |
| 2,6-di-t-butyl-4-methylphenol (BHT, antioxidant) | 128-37-0 | 0.34 |
| 2,6-di-t-butyl-p-methylanisole (antioxidant) | NA | 0.20 |
| 2,4-bis-(dimethylbenzyl)-6-t-butylphenol (antioxidant) | NA | 0.02 |
| hydroquinone monoacetate | NA | 0.15 |
| 4-hydroxy-3-methoxybenzaldehyde (vanillin) | 121-33-5 | 0.01 |
| p-coumaric acid methyl ester | 3943-97-3 | 0.02 |
| pentachlorophenol (PCP, wood preservative) | 87-86-5 | 0.002 |
| 3-methyl-1,8,9-anthracenetriol (3-methylanthralin, Chrysarobin) | 491-59-8 | 11.77 |
| 1,8-dihydroxy-3-methyl-9,10-anthracenedione (Chrysophanol, Chrysophanic acid, 1,8-dihydroxy-3-methyl-1,8-anthraquinone) | 481-74-3 | 10.37 |
| 1,8-dihydroxy-3-(hydroxymethyl)-9,10-anthracenedione (Aloe-Emodin) | 481-72-1 | 0.30 |
| monoacetate derivative of 1,8-dihydroxy-3-(hydroxymethyl)-9,10-anthracenedione (Aloe-Emodin monoacetate) | NA | 0.83 |
| 2,8-dihydroxy-3-methyl-1,4-naphthoquinone (Droserone) | NA | 1.19 |
| bis-flavanoids with m.w.'s 474 ($C_{23}H_{22}O_{11}$), 478 ($C_{22}H_{22}O_{12}$), 490 ($C_{23}H_{22}O_{12}$), 492 ($C_{23}H_{24}O_{12}$), 506 ($C_{23}H_{24}O_{13}$) and 508 ($C_{23}H_{24}O_{13}$) exact chemical structures unknown | NA | 6.27 est. total for DP & LSIMS |

TABLE 10E

| Alcohols | | |
|---|---|---|
| 2-ethyl-1-hexanol | 104-76-7 | 0.65 |
| branched dodecanol isomer | NA | 0.57 |
| 1-dodecanol (dodecyl alcohol) | 112-53-8 | 5.69 |
| 1-tetradecanol (tetradecyl alcohol) | 112-72-1 | 2.14 |
| 2-ethoxy-1-dodecanol | 29718-44-3 | 2.57 |
| 1-hexadecanol (hexadecyl alcohol) | 36653-82-4 | 0.05 |
| 2-ethoxy-1-tetradecanol | NA | 1.09 |

TABLE 10F

| Miscellaneous Compounds | | |
|---|---|---|
| 3,5,5-trimethyl-2-cyclohexene-1-one (isophorone) | 78-59-1 | 0.06 |
| 2,3-dihydro-2,5-dimethyl-4H-1-benzopyran-4-one | 69687-87-2 | 0.08 |
| α-hexylcinnamic aldehyde | 101-86-0 | 0.06 |
| squalene | 7683-64-9 | 0.03 |
| 1-chloro-dodecane (dodecyl chloride) | 112-52-7 | 0.33 |
| sulfur (elemental sulfur six membered ring) | NA | 0.18 |
| sulfur (S-8, cyclic sulfur, orthothrombic sulfur, molecular sulfur) | 10544-50-0 | 0.90 |
| unknown 138 m.w. sulfur-containing compound | NA | 0.05 |
| unknown 216 m.w. aromatic compound | NA | 0.87 |
| unknown 154 m.w. aromatic compound | NA | 0.03 |

TABLE 10F-continued

Miscellaneous Compounds

| | | |
|---|---|---|
| complex mixture of high molecular weight unknown compounds in the range 400–1000, many of these compounds are conjugates of the compounds identified in this study such as glycosides, polar conjugates, high m.w. esters etc. | NA | 6.27 est. total for DP & LSIMS |

Example 6
In vivo Study. Application of the Treatment Solution to a Flaky Skin Mouse The flaky skin mouse (fsn) is a genetically engineered mouse with an autosomal recessive mutation causing the skin to resemble that exhibited in human psoriasis (see Sundberg et al., *J. Vet. Diagn. Invest.* 4:312–17, 1992).

In the homozygous affected flaky skin mouse (fsn/fsn), where the mutation is on both chromosomes, histological features such as marked acanthosis, hyperkeratosis with focal parakeratosis, subcorneal pustules, dermal capillary dilation, and dermal infiltration of inflammatory cells are seen.

Ten affected mice (fsn/fsn) and 10 normal littermate controls (fsn/-) were obtained from The Jackson Laboratory in Bar Harbor, Me. The animals were maintained using standard diet and housing.

The dorsal surface of each animal was shaved. One-half of the dorsal surface received weekly topical treatments of the solution of Example 2, while the other half served as an untreated control. The solution of Example 2 was applied to the skin using a sterile cotton swab. Treatments continued for up to seven weeks. Weekly biopsies of treated and untreated areas were also removed for histological examination. Following the seventh week of treatment, the animals were necropsied for gross pathological changes.

The solution of Example 2 was found to induce dramatic gross and microscopic changes only for the hyperproliferative skin of the affected (fsn/fsn) mice with minimal to no effects noted for the (fsn/-) control mice. Observations by a veterinary dermatopathologist described the skin response of the affected animals as being similar to a "chemical burn." Histologic findings indicated that the keratinocyte growth of the affected mouse skin was markedly reduced, and that the treated skin began to slough off a bit but remained fully attached as a biological bandage allowing healing of the underlying skin. This effect was not observed in the control animals or untreated skin in the affected animals. Results are presented in Table 11.

TABLE 11

Summary of Flaky Skin Mouse Study

| I.D. NUMBER | Phenotype | Histological Assessment | Gross Pathologic Changes | Comments |
|---|---|---|---|---|
| 1 (fsn/fsn) | Flaky skin | Reduction in proliferation of keratinocytes | None observed | |
| 2 (fsn/fsn) | Flaky skin | Reduction in proliferation of keratinocytes | None observed | |
| 3 (fsn/fsn) | Flaky skin | Reduction in proliferation of keratinocytes | None observed | |
| 4 (fsn/fsn) | Flaky skin | Reduction in proliferation of keratinocytes | None observed | |
| 5 (fsn/fsn) | Flaky skin | Reduction in proliferation of keratinocytes | None observed | |
| 6 (fsn/fsn) | Flaky skin | Reduction in proliferation of keratinocytes | None observed | |
| 7 (fsn/fsn) | Flaky skin | Reduction in proliferation of keratinocytes | None observed | |
| 8 (fsn/fsn) | Flaky skin | Reduction in proliferation of keratinocytes | None observed | |
| 9 (fsn/fsn) | Flaky skin | Reduction in proliferation of keratinocytes | None observed | |
| 10 (fsn/fsn) | Confusing phenotype | Marginal change | None observed | Jackson Labs suggest mistyping of animal |
| 11 (+/-) | Normal skin | No change | None observed | |
| 12 (+/-) | Normal skin | No change | None observed | |
| 13 (+/-) | Normal skin | No change | None observed | |
| 14 (+/-) | Normal skin | No change | None observed | |
| 15 (+/-) | Normal skin | No change | None observed | |
| 16 (+/-) | Normal skin | No change | None observed | |
| 17 (+/-) | Normal skin | No change | None observed | |
| 18 (+/-) | Normal skin | No change | None observed | |
| 19 (+/-) | Normal skin | No change | None observed | |
| 20 (+/-) | Normal skin | No change | None observed | |

Example 7
Bioassay—In vivo Study Bioassay

The in vivo study of Example 6 using the flaky skin mouse model was indicative of keratinocyte cell specifically with respect to the activity of the treatment solution compound.

In vitro cell testing is necessary to detect activity with respect to cell type for purposes of developing a bioassay for treatment solution activity, and second to further study results obtained using the flaky skin mice of Example 6. Because human skin contains both keratinocytes and fibroblasts, either of which may be involved in the psoriasis disease process, pure cultures of human fibroblasts were grown from normal adult human skin, keloid scars (hyperproliferative fibroblasts), and commercially available certified pure cultures of normal human adult epidermal keratinocytes. These cell types were tested separately for their growth responses to treatment with the treatment solution of Example 2.

Protocol

Cell growth is measured by examining the amounts of DNA synthesis, for as cells grow and divide, more DNA is produced. Radioactive thymidine is added to the cell culture media. The assay is conducted as follows: Cultured fibroblasts are grown in complete minimal essential medium (CMEM) containing 10% fetal bovine serum as a growth factor source. Epidermal keratinocytes were cultured in the presence of complete keratinocyte growth medium (CKGM) supplemented with bovine pituitary extract, hydrocortisone, and epidermal growth factor (EGF) as a growth factor source.

Healthy growing cells were seeded into Corning 24 well tissue culture plates at a density of $1.0 \times 10^4$ cells per well in 1.0 ml of either CMEM or CKGM depending on cell type. The cells were incubated for 24–36 hours or until they reached 60–70% confluency at 37° C. in the presence of 5% $CO_2$. The medium was then changed to either MEM without the 10% serum or KGM without hydrocortisone or ECF, but leaving the BPE in the media. This allows starvation of the cells, or their regression to a nongrowth phase where although they are not dividing, they remain biochemically active. The cells were allowed to incubate under these conditions for 24 hours. The starving media were then removed and replaced with 1.0 ml/well of complete growth media CMEM or CKGM containing no treatment, treatment solution of Example 2, or a subfraction from Example 4 at a dilution of 1:5000, or solvent alone such as acetic acid or DMSO. Statistically significant numbers of repetitions were performed for each treatment. Additionally 1 $\mu$Ci tritiated thymidine ($^3$H) was also added per well. Following these treatments, the cells were allowed to incubate for 24 hours using identical conditions as above. Following the end of the incubation period, the wells were washed 3 times with phosphate buffered saline (PBS) and fixed with 12.5% trichloroacetic acid (TCA) for 10 minutes followed by methanol for 10 minutes. The plates were air dried and the cells solubilized in 1.0 ml of 0.2 N NaOH at 37° C. for 1 hour. Growth was determined by measuring the level of radioactivity present. This was accomplished by counting 0.9 ml of the solubilized cells in a scintillation counter.

Results

Fibroblasts

Figure 24:
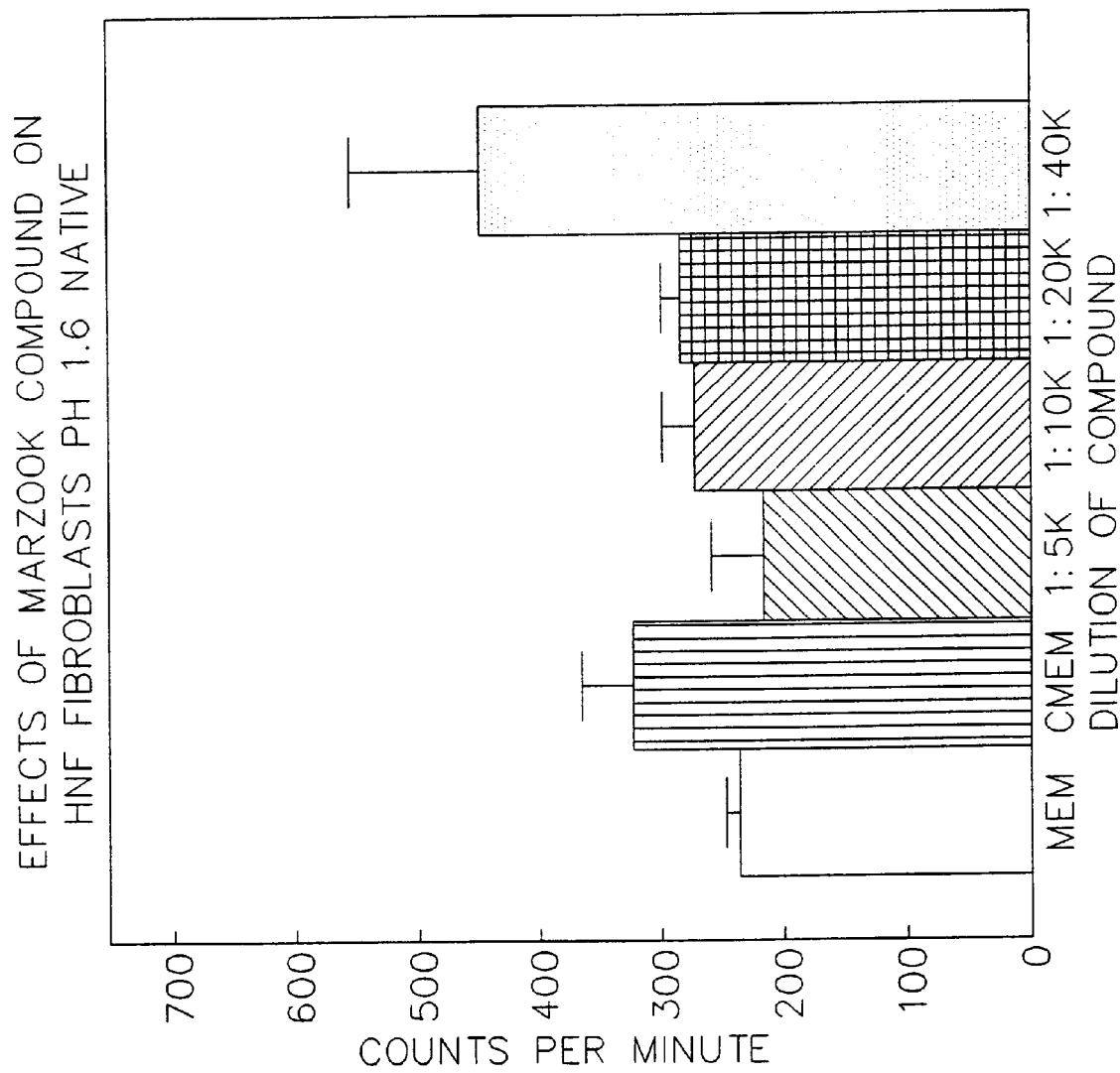
FIG. 24 is a plot showing the effects of the treatment solution of Example 2 on HNF in fibroblasts.

Fibroblasts from normal adult skin and keloid scar were cultured and assayed for effects of the treatment solution on growth as described above. Neither normal nor keloid fibroblasts were inhibited by the treatment solution. A typical graph for these experiments is shown in FIG. 24.

Keratinocytes

The treatment solution of Example 2 was fractioned as in Example 4, with the chemical compositions of those fractions analyzed in Example 5 and results shown in Tables 3–9 above.

Tables 12–14 summarize the percentages of the 4 main active ingredients in each of those fractions, and mean percentages of inhibition in the keratinocyte bioassay for each fraction. Finally, mean percentages of inhibition are normalized to the percentages of each active ingredient in the fractions mentioned above.

TABLE 12

Percentages of 4 Main Active Ingredients in the Treatment Solution of Example 2, Compiled from Tables 3–10

| Fraction | FIG. I REF. NO. | 3-methyl anthralin | chrysa- robi | aloe- emodin | aloe-emodin monoacetate |
|---|---|---|---|---|---|
| XAD-2 Resin DCM Eluate | 23 | 5.86% | 11.76% | 0.14% | 2.23% |
| XAD-2 Resin MeOH Eluate- DCM-Insol. | 26 | 27.82% | 12.78% | 0% | 0% |
| Hydrolyzed Z-92 XAD Resin-MeOH Eluate DCM Insol. | 29 | 0.42% | 4.71% | 0% | 0% |
| Z-92 Carboxy- lic Acid Fx | 28 | 0.55% | 1.3% | 0% | 0% |
| Precipitate From Neutral/ Phenol Fx | 36 | 19.69% | 57.41% | 0% | 0% |
| Neutral/Phenol Silica Gel MeOH Eluate | 31 | 2.57% | 5.7% | 3.82% | 1.34% |
| Neutral/Phenol Silica Gel DCM Eluate | 31 | 5.06% | 15.00% | 0% | 6.24% |
| Crude Z-92 | 10 | 11.77% | 10.37% | 0.30% | 0.83% |

TABLE 13

Fraction Analysis Summary Results — % Growth Inhibition of Keratinocytes by Fraction

| Fraction Ref. No. From FIG. 1 | Mean % Inhibit. | 7/12 | 7/21 | 7/28 | 8/3 | 8/28 | 9/14 | 9/15 | 10/6 | 10/13 |
|---|---|---|---|---|---|---|---|---|---|---|
| 23 | 62% | | | 60% | | | | 64% | | |
| 26 | 50% | 51% | | 44% | | | | 56% | | |
| 29 | 7% | | | | | | | | | 7% |
| 28 | 40% | 51% | | 35% | | | | 35% | | |
| 36 | 63% | | | | 50% | | | 76% | | |
| 31 | 30% | | | | 20% | | | 39% | | |
| 31 | 92% | | | | 94% | 99% | 98% | 80% | 94% | 89% |
| ?? | 21% | | | | | 17% | | | 24% | |
| ?? | 17% | | | | | 15% | | | 18% | |
| ?? | 16% | | | | | | | | 16% | |
| 10 | 77% | | | 77% | | 79% | 84% | | 69% | |
| ?? | 94% | | | | | | | 94% | | |

TABLE 14

Percent Inhibition per Percentage of Ingredient in Fraction for 4 Main Active Ingredients in the Treatment Solution of Example 2 (Calculated From Mean % Inhibition from Table 13)

| Fraction Description From FIG. 1 | Fraction Ref. No. From FIG. 1 | 3-methyl anthralin | chrysarobi | aloe-emodin | aloe-emodin monoacetate |
|---|---|---|---|---|---|
| XAD-2 Resin DCM Eluate | 23 | 10.58% | 5.27% | 443% | 28% |
| XAD-2 Resin MeOH Eluate-DCM-Insol. | 26 | 1.79% | 3.91% | 0% | 0% |
| Hydrolyzed Z-92 XAD Resin-MeOH Eluate DCM Insol. | 29 | 16.66% | 1.48% | 0% | 0% |
| Z-92 Carboxylic Acid Fx | 28 | 72.72% | 30.76% | 0% | 0% |
| Precipitate From Neutral/Phenol Fx | 36 | 3.19% | 1.15% | 0% | 0% |
| Neutral/Phenol Silica Gel MeOH Eluate | 31 | 11.67% | 5.26% | 7.85% | 22.38% |
| Neutral/Phenol Silica Gel DCM Eluate | 31 | 18.18% | 6.13% | 0% | 14.74% |
| Crude Z-92 | 10 | 6.54% | 7.42% | 256.6% | 92.77% |

Example 8

Neutralization Study

As the pH of the treatment solution of Example 2 is very acidic, studies were undertaken to neutralize the pH to 7.0 in order to examine inhibitory properties in the neutral state. Crude treatment solution was adjusted to pH 7.0 with 1.0 N NaOH. Keratinocytes were assayed for growth in the presence of the neutralized extract using bioassay methodology as described above, except that neutralized treatment solution was added as the test compound at a dilution of 1:5000.

Results of this analysis indicated that neutralization removes activity of the treatment solution. While not wishing to be limited by theory, it is hypothesized that the addition of acetic acid during the preparation sequence for the treatment solution may acetylate reactive molecules, conferring additional biological activity. This may confer increased abilities to enter cells, etc. Neutralization of such entities by raising the pH to 7.0 may render the active moieties inactive, as reflected by the dramatically decreased activity observed with these studies.

Example 9

Protein Study

This Example examines whether or not any proteins were present in the treatment solution of Example 2. Toward this end, treatment solution was denatured at 65° C. in the presence of sodium dodecyl sulfate (SDS) and electrophoresed on 12% polyacrylamide gels (PAGE) in the presence of SDS.

Following electrophoretic analysis and staining with Coomassie blue, no proteins were evident on visual inspection of the gel.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty that reside in the present invention, including all features that would be treated as equivalents thereof by those skilled in the art to which this invention pertains.

What is claimed is:

1. A composition for the treatment of psoriasis comprising an effective amount of an extract from a root portion of an *Asphodelus Microcarpus* plant and acetic acid.

2. The composition recited in claim 1, wherein the extract and the acetic acid are present in a volume proportion in the range of 1:20 to 20:1.

3. The composition recited in claim 1, wherein the extract and the acetic acid are present in a volume proportion of 4:1.

4. The composition recited in claim 3, further comprising brimstone.

5. A method for treating psoriasis in a mammal comprising the steps of:
   providing an *Asphodelus Microcarpus* plant;
   extracting a liquid from a root of the plant; and
   applying an effective amount of the liquid to an area of skin of the mammal affected by psoriasis.

6. The method recited in claim 5, further comprising mixing the liquid with acetic acid.

7. The method recited in claim 6, wherein the mixing step comprises mixing the liquid with acetic acid in a volume ratio in the range of 20:1 to 1:20.

8. The method recited in claim 7, wherein the mixing step comprises mixing the liquid with acetic acid in a volume ratio of approximately 4:1.

9. The method recited in claim 6, further comprising mixing the liquid-acetic acid mixture with brimstone.

10. The method recited in claim 5, wherein the extracting step comprises extracting a liquid comprising the compounds 3-methylanthralin, chrysophanol, aloe-emodin, and aloe-emodin monoacetate.

11. The method recited in claim 6, wherein the applying step comprises applying the mixture to the affected area of skin once per day for a duration sufficient to alleviate the symptoms of psoriasis.

12. The method recited in claim 11, wherein the duration comprises a range of 14 to 56 days.

13. The method recited in claim 5, wherein the extracting step comprises extracting a liquid comprising the compounds 3-methylanthralin, chrysophanol, aloe-emodin, and aloe-emodin monoacetate.

* * * * *